(12) United States Patent
Yokoyama et al.

(10) Patent No.: US 9,605,300 B2
(45) Date of Patent: Mar. 28, 2017

(54) DEVICE FOR GENOTYPIC ANALYSIS AND METHOD FOR GENOTYPIC ANALYSIS

(71) Applicant: Hitachi High-Technologies Corporation, Tokyo (JP)

(72) Inventors: Toru Yokoyama, Tokyo (JP); Motohiro Yamazaki, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 93 days.

(21) Appl. No.: 14/652,922

(22) PCT Filed: Dec. 4, 2013

(86) PCT No.: PCT/JP2013/082609
§ 371 (c)(1),
(2) Date: Jun. 17, 2015

(87) PCT Pub. No.: WO2014/097888
PCT Pub. Date: Jun. 26, 2014

(65) Prior Publication Data
US 2015/0337360 A1 Nov. 26, 2015

(30) Foreign Application Priority Data
Dec. 17, 2012 (JP) ................. 2012-274672

(51) Int. Cl.
*G01J 3/30* (2006.01)
*C12Q 1/68* (2006.01)
(Continued)

(52) U.S. Cl.
CPC ........... *C12Q 1/68* (2013.01); *G01N 21/6428* (2013.01); *G01N 21/6456* (2013.01);
(Continued)

(58) Field of Classification Search
CPC ........ C12Q 1/68; G01N 27/447; G01N 21/64; G06F 19/18; G01J 3/44
See application file for complete search history.

(56) References Cited

U.S. PATENT DOCUMENTS

2002/0009741 A1  1/2002  Simpson et al.
2002/0090630 A1  7/2002  Hazama
(Continued)

FOREIGN PATENT DOCUMENTS

JP  2002-55080 A  2/2002
JP  2003-270206 A  9/2003
(Continued)

OTHER PUBLICATIONS

Extended European Search Report received in corresponding European Application No. 13865484.3 dated Sep. 22, 2016.
(Continued)

*Primary Examiner* — Abdullahi Nur
(74) *Attorney, Agent, or Firm* — Mattingly & Malur, PC

(57) ABSTRACT

A technique for performing spectral calibration simultaneously with electrophoresis of an actual sample to be analyzed, without performing electrophoresis using a special matrix standard which is time-consuming and costly, is provided. The device for genotypic analysis is characterized by obtaining reference fluorescence spectra using a size standard and an allelic ladder, which provide information concerning known DNA fragments used for electrophoresis of an actual sample, and is characterized by performing spectral calibration for a capillary in which the allelic ladder is not used by detecting a shift amount of the fluorescence spectra of the size standard and shifting the reference fluorescence spectra using the shift amount to determine fluorescence spectra.

12 Claims, 30 Drawing Sheets

(51) Int. Cl.
*G06F 19/18* (2011.01)
*G01N 27/447* (2006.01)
*G01N 21/64* (2006.01)

(52) U.S. Cl.
CPC ..... *G01N 27/447* (2013.01); *G01N 27/44726* (2013.01); *G06F 19/18* (2013.01); *G01N 2021/6417* (2013.01); *G01N 2021/6439* (2013.01); *G01N 2021/6441* (2013.01)

(56) References Cited

U.S. PATENT DOCUMENTS

| | | |
|---|---|---|
| 2004/0110137 A1 | 6/2004 | Hirata et al. |
| 2006/0231400 A1* | 10/2006 | Inaba ............... G01N 27/44782 204/452 |
| 2009/0228245 A1 | 9/2009 | Gilbert et al. |
| 2011/0120869 A1 | 5/2011 | Pang |
| 2012/0267247 A1 | 10/2012 | Tan et al. |

FOREIGN PATENT DOCUMENTS

| | | |
|---|---|---|
| JP | 2005-31051 A | 2/2005 |
| JP | 3690271 B2 | 6/2005 |
| JP | 2008-545956 A | 12/2008 |
| JP | 2011-30502 A | 2/2011 |
| WO | 2007/137320 A2 | 12/2007 |

OTHER PUBLICATIONS

Schumm, J. W., "Why Use a Size Marker and Allelic Ladders in STR Analysis?" Geneprint (TM) Products, Retrieved from the Internet, URL: https://www.promega.com/~/media/files/resources/profiles in dna/102/why use a size marker and allelic ladders in str analysis.pdf?la=en, Jan. 1997, pp. 11-13.

* cited by examiner

FIG. 15

| Dye | Locus | Allele | Length | Min | Max |
|---|---|---|---|---|---|
| 6FAM | D10S1248 | 8 | 77 | -0.5 | 0.5 |
| | | 9 | 81 | -0.5 | 0.5 |
| | | 10 | 85 | -0.5 | 0.5 |
| | | 11 | 89 | -0.5 | 0.5 |
| | | 12 | 93 | -0.5 | 0.5 |
| | | 13 | 97 | -0.5 | 0.5 |
| | | 14 | 101 | -0.5 | 0.5 |
| | | 15 | 105 | -0.5 | 0.5 |
| | | 16 | 109 | -0.5 | 0.5 |
| | | 17 | 113 | -0.5 | 0.5 |
| | | 18 | 117 | -0.5 | 0.5 |
| NED | D22S1045 | 8 | 80 | -0.5 | 0.5 |
| | | 9 | 83 | -0.5 | 0.5 |
| | | 10 | 86 | -0.5 | 0.5 |
| | | ... | ... | ... | ... |

DEVICE FOR GENOTYPIC ANALYSIS AND METHOD FOR GENOTYPIC ANALYSIS

TECHNICAL FIELD

The present invention relates to a device for genotypic analysis using electrophoresis and a method for genotypic analysis.

BACKGROUND ART

At present, DNA typing by analyzing DNA polymorphism is widely employed for purposes of criminal investigations, determination of a blood relation and the like. Nucleotide sequences of DNA of individuals of a same species are similar to each other but are partially different. Such diversity of nucleotide sequences of DNA observed among individuals is called DNA polymorphism, which affects the formation of an individual difference at the genetic level.

One type of DNA polymorphism is a short tandem repeat (STR) or a microsatellite. An STR is a characteristic sequence pattern of a short sequence of about two bases to seven bases repeated several to several dozen times, and it is known that the number of repeating units varies with the individual. Analysis of the combination of numbers of repeating units of STRs at specific loci is called STR analysis.

STR analysis utilizing the property that the combination of numbers of repeating units of STRs varies with the individual is used for DNA typing for the purpose of criminal investigations and the like. FBI (the Federal Bureau of Investigation) and the International Criminal Police Organization have defined ten or more STR loci used for DNA typing as DNA markers and analyze patterns of numbers of repeating units of these STR sequences. Because a difference in the number of STR repeating units arises due to the difference in the allele, a number of repeating units of STR in a DNA marker is referred to as an allele below.

In order to extract a certain amount of DNA of an STR locus used as a DNA marker, PCR (Polymerase Chain Reaction) is performed. PCR is a technique for obtaining a certain amount of a sample of target DNA by specifying certain nucleotide sequences called primer sequences at both ends of the target DNA and repeatedly amplifying only the DNA fragment between the primer sequences.

Electrophoresis is performed to measure the length of the target DNA fragment obtained by PCR. Electrophoresis is a method for separating DNA fragments using the phenomenon that the migration speed in a charged migration path varies with the DNA fragment length (the migration speed is lower as the DNA fragment is longer). As means of electrophoresis, capillary electrophoresis using a capillary as the migration path has been often used recently.

In capillary electrophoresis, a thin tube called a capillary is filled with a migration medium such as a gel, and sample DNA fragments are allowed to migrate through the capillary. The DNA fragment length is determined by measuring the time required for the sample to migrate a certain distance (generally from one end of the capillary to the other). Each sample, namely each DNA fragment, is labeled with a fluorescent dye, and the fluorescence signal from the migrated sample is detected with an optical detector placed at the end of the capillary.

Fluorescent dyes used for labeling different DNA fragments have different spectra, which are not sharp and overlap with each other. Therefore, in the optical detector at the end of the capillary, when DNA fragments labeled with different fluorescent dyes have similar fragment lengths, the spectrum obtained with the optical detector is a linear sum of the spectra of the different fluorescent dyes (referred to as fluorescence spectra below), namely a weighted sum. Accordingly, in order to determine the signal intensities of the respective fluorescent dyes, the linear coefficients of the spectra of the fluorescent dyes constituting the spectrum, that is the weighed values, should be determined from the spectrum obtained with the optical detector. The weighed values correspond to the signal intensities of the respective fluorescent dyes.

In order to determine the signal intensities of the fluorescent dyes, the respective fluorescence spectra should be known in advance. Originally, each fluorescence spectrum is determined exclusively by the fluorescent dye and the migration medium, irrespective of the apparatus, but in an actual apparatus, a fluorescence spectrum imaged on the optical detector shifts due to the positional relation of the capillary and the fluorescence signal detector. Accordingly, when the capillary is replaced, fluorescence spectra must be measured in advance before electrophoresis of the target sample, and calibration for adjusting the positions of the fluorescence spectra (referred to as spectral calibration below) is necessary. In this regard, when electrophoresis is performed simultaneously for two or more samples using a capillary array containing aligned capillaries, it is necessary to measure the fluorescence spectra of each capillary.

Next, an example of spectral calibration of the conventional technology is explained, referring to FIG. 2 and FIG. 3.

FIG. 2 is a figure showing an example of images formed on the optical detector placed at capillary ends. Excitation light of a fluorescent dye obtained by irradiating a capillary end with laser light of a specific wavelength is separated in the wavelength direction with a diffraction grating, and the image is detected with a camera device such as a CCD. The figure shows diffraction grating images obtained by irradiating a capillary array containing eight aligned capillaries ((1) to (8)) with laser light (at the bottom of the figure). In the figure (at the bottom), the vertical axis shows the alignment direction of the capillaries and the horizontal axis shows the wavelength direction, and the figure (on top) is a figure showing the signal intensity along the A-A' direction of capillary (4) shown at the bottom. The figure (on top) shows the signal intensity distribution, where the vertical axis corresponds to the brightness value indicating the signal intensity and the horizontal axis corresponds to the wavelength. As shown in the figure (on top), the spectrum of a capillary can be obtained as a waveform, where the vertical axis corresponds to the signal intensity in the capillary and the horizontal axis corresponds to the wavelength.

In this regard, FIG. 2 shows an example of spectra measured continuously (as a matter of fact, discretely per pixel) using a diffraction grating, but in practice, the data may be obtained by sampling the spectra above at longer wavelength intervals. For example, as shown in the figure, the brightness values may be obtained only at 20 wavelengths ($\lambda(0)$ to $\lambda(19)$) for each capillary. In addition, averages of the brightness values at wavelengths around $\lambda(0)$ to $\lambda(19)$ may be taken.

Moreover, an image may be taken after rapidly changing to a filter which filters only the wavelength region in which the sensitivity to a fluorescent dye is the highest, without using any diffraction grating. Alternatively, camera devices and filters corresponding to fluorescent dyes may be provided to the number of the fluorescent dyes, thereby taking images of the respective fluorescent dyes at the same time. Since such a case corresponds to sampling of spectra at the sample positions corresponding to the respective fluorescent dyes from the spectra shown in the figure, the means of the invention below can be similarly applied.

FIG. 3 is a flowchart of the spectral calibration process. In a step 301, a sample called a matrix standard is subjected to electrophoresis. A matrix standard is a reagent used for performing electrophoresis for the purpose of obtaining fluorescence spectra and obtaining the matrix explained below.

Here, a summary of the matrix standard is given using FIGS. 4A and 4B. FIGS. 4A and 4B are on the supposition that fluorescence spectra of five kinds of fluorescent dye (LIZ, PET, NED, VIC and 6FAM) are obtained. In FIG. 4A, the vertical axis shows the fluorescence intensity and the horizontal axis shows the time, and the five kinds of fluorescent dye have sharp peaks at the times corresponding to the respective fluorescent dyes. Therefore, in order to obtain the fluorescence spectrum of a fluorescent dye, the spectrum at the time at which only the fluorescent dye emits light (in FIG. 4A, t0, t1, t2, t3 and t4) should be obtained. Thus, with respect to the matrix standard, five kinds of DNA fragment with different lengths are labeled with different fluorescent dyes. The information concerning the lengths of the DNA fragments corresponding to the respective fluorescent dyes or the order of the lengths is known.

Next, in a step 302, the intensities of the fluorescent dyes are calculated from the spectra at the respective times obtained by electrophoresis in the step 301. Details of this process will be described below. This process may be conducted at each of the scanning times or after storing spectral data at a certain time interval. An example of waveforms of the fluorescence intensities obtained is shown in FIG. 4A.

In FIG. 4A, waveforms of the signal intensities of the fluorescent dyes (referred to as fluorescence intensities below) are shown in one graph, where the horizontal axis corresponds to the scanning time. There are peaks in the fluorescence intensity waveforms, and the peak times correspond to the DNA fragment lengths. As described above, since DNA fragments with different lengths are labeled with different fluorescent dyes with respect to the matrix standard, one fluorescent dye emits light individually at each peak time (t0, t1, t2, t3 and t4).

Thus, in a step 303, peak times of the waveforms of the fluorescence intensities (signal intensities) of FIG. 4A are detected. This peak detection process will be described below. FIG. 4A shows the results that peak times t0, t1, t2, t3 and t4 have been obtained. As described above, since the order of appearing peak times that correspond to the respective fluorescent dyes is known, the kinds of fluorescent dye corresponding to the respective peak times can be identified. The figure shows the results that LIZ, PET, NED, VIC and 6FAM individually emit light at times t0, t1, t2, t3 and t4, respectively. In other words, the spectra at the times correspond to the fluorescence spectra of the respective fluorescent dyes. Therefore, the spectra at the respective peak times should be obtained (see FIG. 4B).

Then, in a step 304, the matrix described below is calculated using the fluorescence spectra. The matrix is a matrix for obtaining the intensities of the respective fluorescent dyes from the spectral waveforms obtained with a detector. The process of calculating the matrix is called spectral calibration. When there are two or more capillaries, it is necessary to calculate the matrix for each of the capillaries. Moreover, it is necessary to perform spectral calibration every time a capillary is installed or a part is changed.

CITATION LIST

Patent Literature

[PTL 1] US2009/0228245

SUMMARY OF INVENTION

Technical Problem

However, since the spectral calibration of the conventional technology requires separate electrophoresis of the matrix standard prior to electrophoresis of an actual sample to be analyzed, there has been a problem in that effort and time are required. In addition, since the matrix standard, which is consumable, is necessary, there has been a problem concerning the increased price for users.

Therefore, an object of the invention is to provide a technique for performing spectral calibration simultaneously with electrophoresis of an actual sample to be analyzed without performing electrophoresis using a special matrix standard which requires effort and is costly.

Solution to Problem

As means for achieving the object, the device for genotypic analysis of the invention is characterized by obtaining reference fluorescence spectra using a size standard and an allelic ladder which provide information concerning known DNA fragments used for electrophoresis of an actual sample.

Moreover, the device for genotypic analysis is characterized by performing spectral calibration for a capillary in which the allelic ladder is not used, by detecting a shift amount of the fluorescence spectrum of the size standard and shifting the reference fluorescence spectra using the shift amount to determine fluorescence spectra.

Furthermore, the device for genotypic analysis is characterized by performing spectral calibration for a capillary in which the allelic ladder is not used, without using the shift amount but directly using the results of electrophoresis of the actual sample.

Advantageous Effects of Invention

According to the invention, spectral calibration can be performed in a short time at a low cost because electrophoresis using a special matrix standard is not necessary.

BRIEF DESCRIPTION OF DRAWINGS

[FIG. 15] A figure for explaining an example of allele information contained in an allelic ladder.

DESCRIPTION OF EMBODIMENTS

The invention provides a technique for performing spectral calibration simultaneously with electrophoresis of an actual sample.

Examples are explained below, referring to the attached drawings. However, attention should be paid to the points that the Examples are merely examples for achieving the invention and do not limit the technical scope of the invention. Moreover, a same component in the figures is given a same reference number.

Example 1

Figure 1:
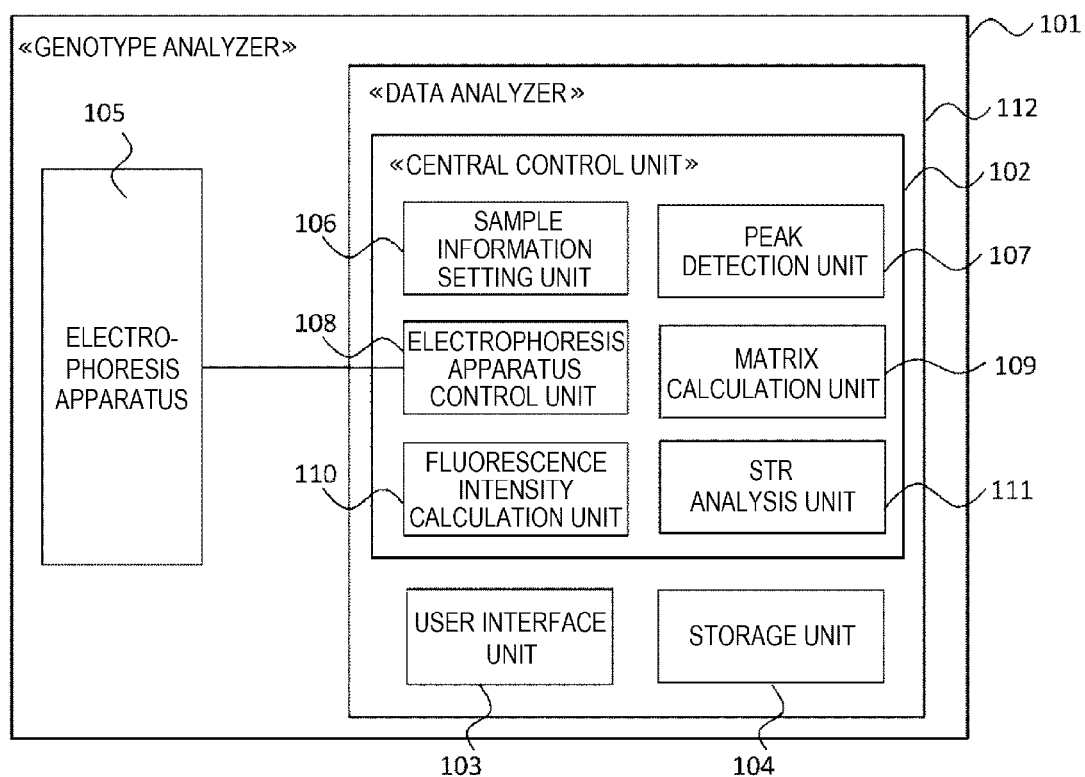
[FIG. 1] A figure showing an outline constitution of the genotype analyzer (or device for genotypic analysis) according to Example 1.

A constitution of the genotype analyzer (or device for genotypic analysis) of Example 1 of the invention is shown in FIG. 1. A genotype analyzer 101 is composed of a data analyzer 112 and an electrophoresis apparatus 105. The data analyzer 112 is composed of a central control unit 102 which controls electrophoresis and processes data, a user interface unit 103 which provides information for the user and inputs information from the user and a storage unit 104 which stores data and settings information of the apparatus.

The central control unit 102 is composed of a sample information setting unit 106, an electrophoresis apparatus control unit 108, a fluorescence intensity calculation unit 110, a peak detection unit 107, a matrix calculation unit 109 and an STR analysis unit 111. The respective functions will be described below.

Figure 5:
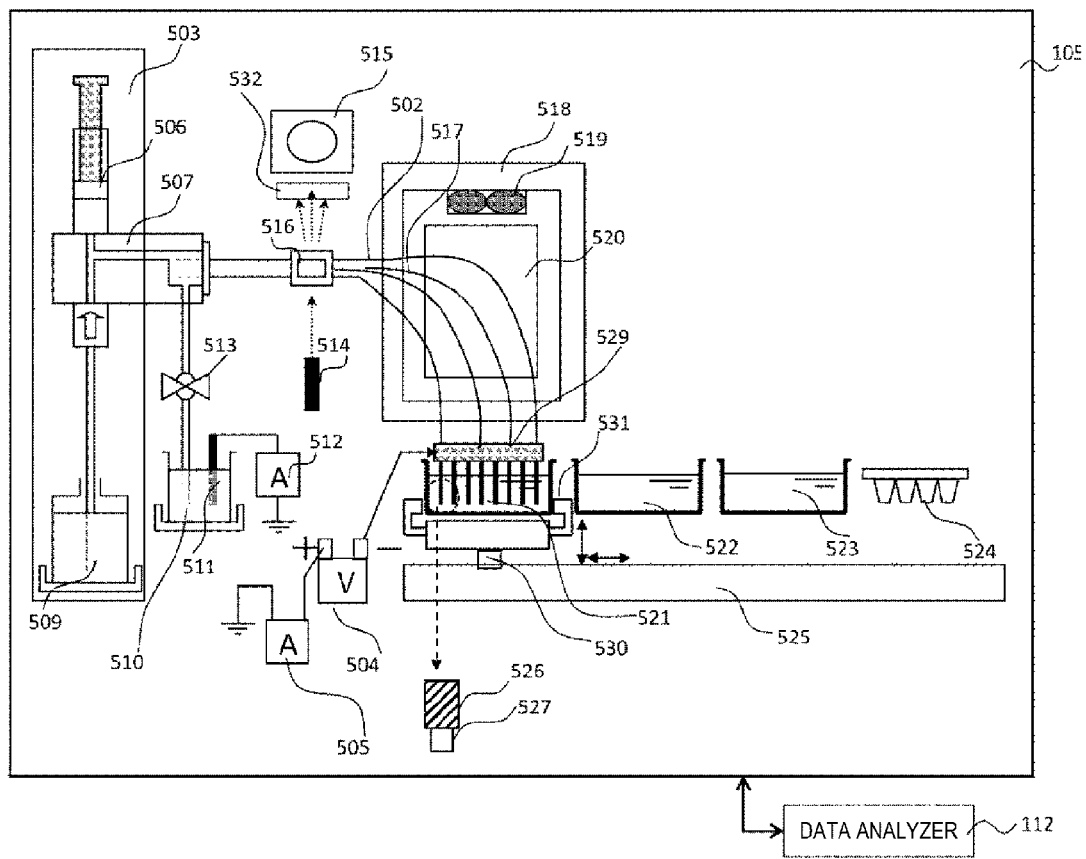
[FIG. 5] A figure showing an outline constitution of the electrophoresis apparatus according to Example 1.

FIG. 5 is a schematic diagram of the electrophoresis apparatus 105. A constitution of the electrophoresis apparatus 105 is explained, referring to FIG. 5.

The electrophoresis apparatus 105 is composed of a detection unit 516 for optically detecting a sample, a thermostatic bath 518 for keeping a capillary at a constant temperature, a carrier 525 for carrying various vessels to a capillary cathode end, a high voltage power supply 504 for applying high voltage to the capillary, a first ammeter 505 for detecting a current generated from the high voltage power supply, a second ammeter 512 for detecting a current flowing to the anode-side electrode, a capillary array 517 composed of one or more capillaries 502 and a pumping mechanism 503 for injecting a polymer to a capillary.

The capillary array 517 is an exchangeable member containing two or more (for example, eight) capillaries and contains a load header 529, the detection unit 516 and a capillary head. The capillary array 517 is replaced with a new capillary array when a capillary is damaged or the quality deteriorates.

Each capillary is made of a glass tube having an internal diameter of several dozen to several hundred microns and an external diameter of several hundred microns, and its surface is coated with a polyimide to improve the strength. In this regard, however, the polyimide coating is removed from a light irradiation part which is irradiated with laser light, so that light emitted from inside easily leaks to the outside. The inside of the capillary 502 is filled with a separation medium for causing a difference in the migration speed during electrophoresis. There are fluid and non-fluid separation media, but a fluid polymer is used in this Example.

The detection unit 516 is a member which obtains information depending on the sample. When excitation light is applied from a light source 514 to the detection unit 516, information light (fluorescence having a wavelength depending on the sample) is generated from the sample and emitted. The information light is separated in the wavelength direction with a diffraction grating 532, and the separated information light is detected with an optical detector 515 to analyze the sample.

Each capillary cathode end 527 is fixed through a hollow electrode 526 made of metal, and the tip of the capillary of about 0.5 mm stands out from the hollow electrode 526. All of the hollow electrodes provided for the capillaries are combined and attached to the load header 529. Moreover, all the hollow electrodes 526 are electrically connected to the high voltage power supply 504 installed in the apparatus and works as cathodes during electrophoresis, sample injection and the like where voltage should be applied.

The capillary ends which are opposite to the capillary cathode ends 527 (the other ends) are combined with the capillary head. The capillary head can be connected to a block 507 in a pressure resistant, airtight manner. A syringe 506 fills the capillaries with a fresh polymer from the other ends. The polymer in the capillaries is changed for every measurement to improve the measurement property.

The pumping mechanism 503 is composed of the syringe 506 and a mechanism for applying pressure to the syringe. The block 507 is a connection unit for connecting the syringe 506, the capillary array 517, an anode buffer vessel 510 and a polymer vessel 509.

An optical detection unit is composed of the light source 514 for irradiating the detection unit 516, the optical detector 515 for detecting light emitted in the detection unit 516 and the diffraction grating 532. When a sample in a capillary separated by electrophoresis is detected, the detection unit 516 of the capillary is irradiated with the light source 514, and light emitted from the detection unit 516 is separated with the diffraction grating 532 and detected with the optical detector 515.

The thermostatic bath 518 is covered with a heat insulating material to keep the internal temperature of the thermostatic bath constant, and the temperature is controlled with a heating/cooling mechanism 520. A fan 519 circulates and agitates the air in the thermostatic bath, and the temperature of the capillary array 517 is kept uniform and constant at every position.

The carrier 525 has three electric motors and linear actuators and is movable along three axes of top to bottom, left to right and depth directions. At least one or more vessels can be placed on a mobile stage 530 of the carrier 525. The mobile stage 530 has an electric grip 531, which can grip or release the vessels. Thus, a buffer vessel 521, a washing vessel 522, a waste fluid vessel 523 and a sample vessel 524 can be carried to the capillary cathode ends 527 according to the need. In this regard, an unnecessary vessel is stored in a certain storage place in the apparatus.

The electrophoresis apparatus 105 is connected to the data analyzer 112 through a signal cable and used in this state. The operator can control the functions of the apparatus through the data analyzer 112 and give and receive data detected with the detector in the apparatus.

Figure 6:
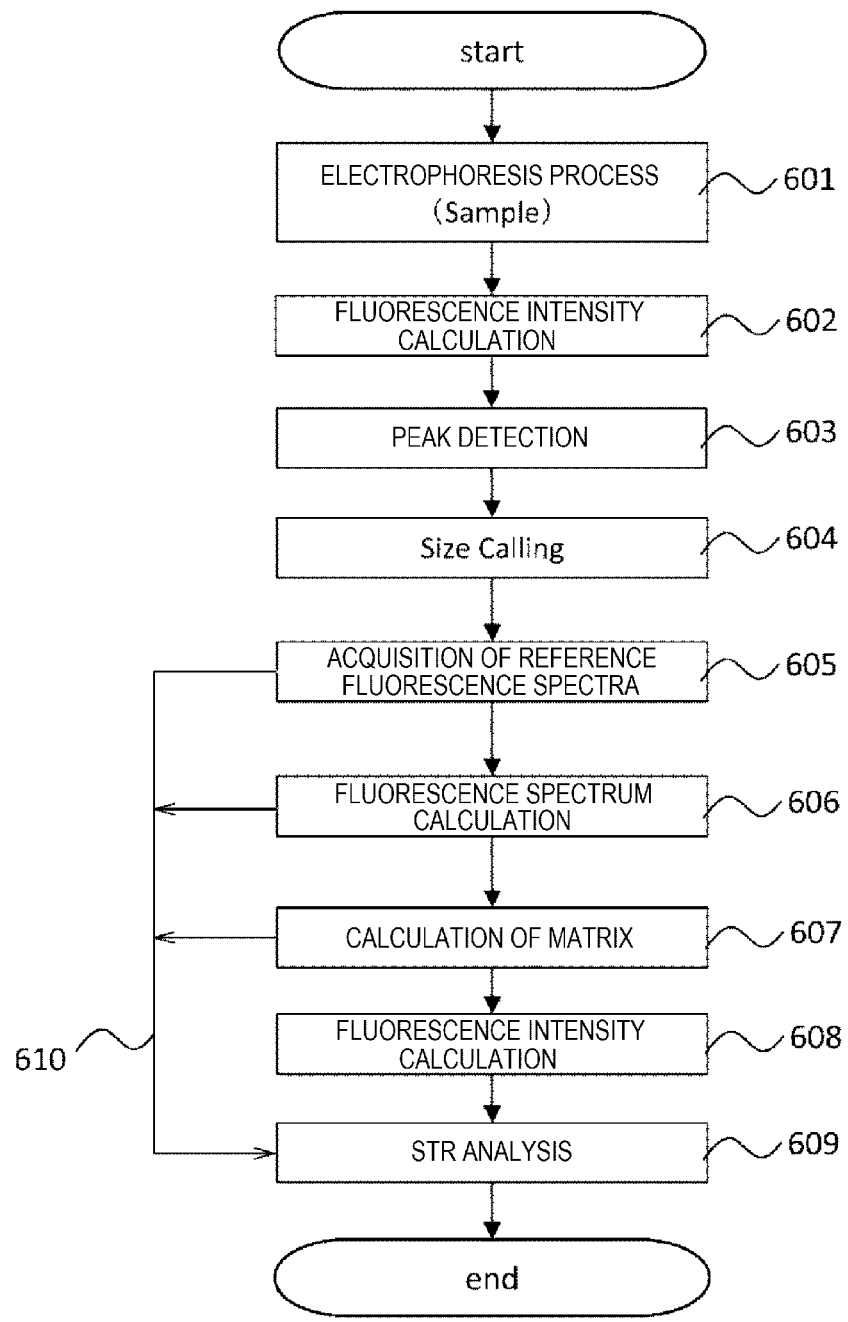
[FIG. 6] A flowchart of the process of the genotype analyzer according to Example 1.

A summary of the process flow of the genotype analyzer is explained by this Example, referring to FIG. 6.

First, an electrophoresis process is conducted for an actual sample to be analyzed in a step 601.

Next, in a step 602, fluorescence intensities of respective fluorescent dyes are calculated from spectral waveform data obtained by electrophoresis.

Then, in a step 603, peaks are detected from the waveforms of the fluorescence intensities.

Next, in a step 604, the relation between the time and the DNA fragment length is determined by mapping the obtained peak times and information concerning known DNA fragment lengths of a size standard. This process is called size calling.

After this, fluorescence spectra of a reference capillary are obtained in a step 605. Here, the reference capillary refers to the capillary in which electrophoresis of an allelic ladder, which will be described below, is performed.

Next, in a step 606, fluorescence spectra of another capillary are calculated.

Then, in a step 607, a matrix is calculated using the obtained fluorescence spectra.

In a step 608, the fluorescence intensities of the respective fluorescent dyes are calculated using the obtained matrix.

Then, in a step 609, STR analysis is conducted using the obtained fluorescence intensity data.

In this regard, the step 610 in the flowchart shown in FIG. 6 indicates that the intervening steps are sometimes skipped, thereby directly proceeding to the step 609 to conduct STR analysis. A specific case thereof will be described below.

Details of the processes in the steps 601 to 609 are described below, referring to the drawings.

<Explanation of the Step 601>

Figure 7:
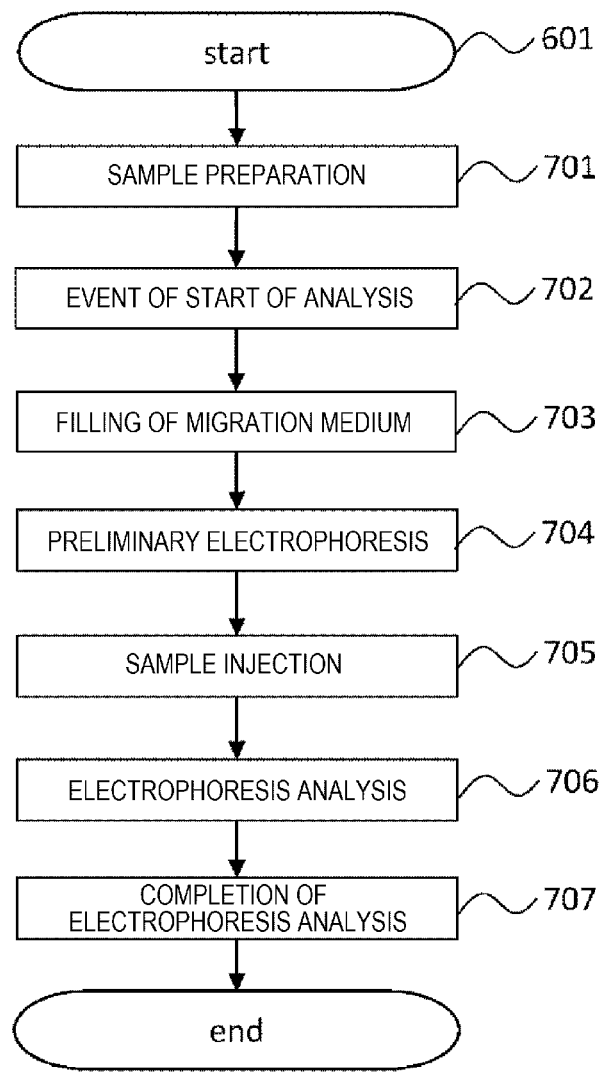
[FIG. 7] A flowchart of the electrophoresis process according to Example 1.

FIG. 7 shows the flow of the electrophoresis process of an actual sample in the step 601.

Basic procedures of electrophoresis can be roughly classified into sample preparation (a step 701), the start of analysis (a step 702), filling of a migration medium (a step 703), preliminary electrophoresis (a step 704), sample injection (a step 705) and electrophoresis analysis (a step 706).

The processes in the steps are explained in detail below.

Step 701: The operator of the apparatus sets samples and regents to the apparatus as the sample preparation (the step 701) before the start of the analysis. More specifically, the buffer vessel 521 and the anode buffer vessel 510 shown in FIG. 5 are first filled with a buffer solution which will be a part of a current path. Examples of the buffer solution are commercial electrolytic solutions for electrophoresis which various companies provide. Moreover, samples to be analyzed are dispensed to the wells of a sample plate 524. An example of the samples is PCR-amplified DNA. Furthermore, a washing solution for washing the capillary cathode ends 527 is poured to the washing vessel 522. An example of the washing solution is pure water. In addition, a separation medium for electrophoresis of the samples is poured into the syringe 506. Examples of the migration medium are commercial polyacrylamide-based separation gels for electrophoresis which are provided by various companies. Moreover, when the deterioration of the capillaries 502 is expected or when the length of the capillaries 502 should be changed, the capillary array 517 is replaced.

Here, the samples which are set in the sample plate 524 are a positive control, a negative control and an allelic ladder as well as the actual sample of DNA to be analyzed, and electrophoresis of the samples is performed in different capillaries. An example of the positive control is PCR-amplified fragments of known DNA, and the positive control is a sample for the control experiment to confirm that DNA fragments have been amplified properly by PCR. The negative control is a PCR product which does not contain DNA and is a sample for the control experiment to confirm that PCR-amplified fragments are not contaminated with DNA of the operator, dust or the like.

The allelic ladder is an artificial sample containing many alleles which may be generally contained in DNA markers and is usually provided by reagent manufacturers as a reagent kit for DNA typing. The allelic ladder is used for the purpose of fine adjustment of the relation between the DNA fragment length and the allele of each DNA marker. The allelic ladder will be described below.

Figure 12A:
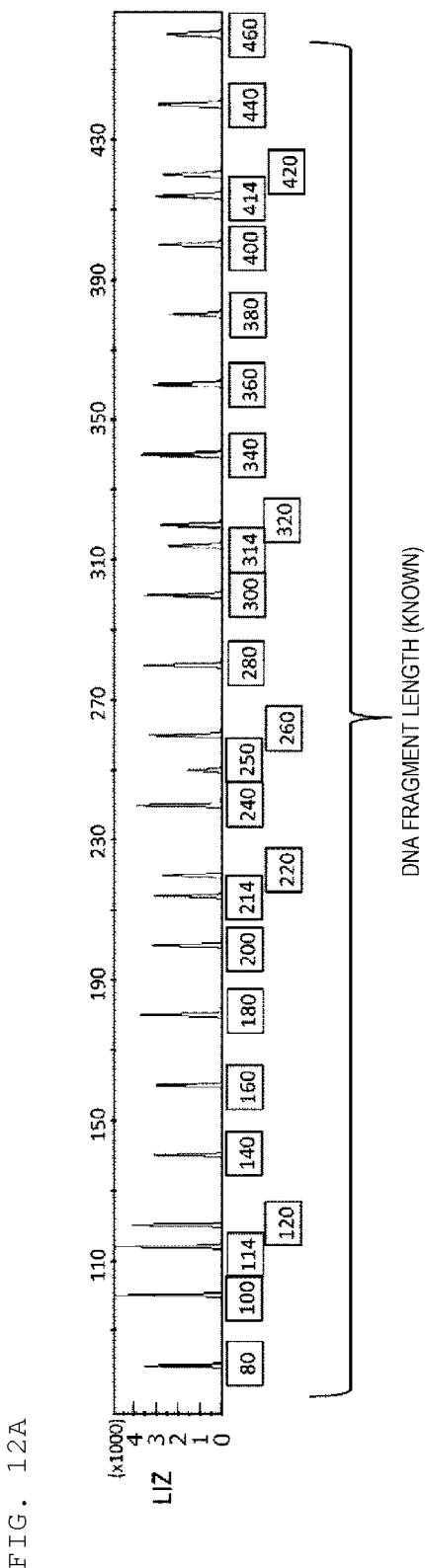
[FIG. 12A] A figure for explaining a summary of size calling according to Example 1.

The actual sample, the positive control, the negative control and the allelic ladder are all mixed with known DNA fragments labeled with a fluorescent dye, which are called a size standard. The kind of fluorescent dye assigned to the size standard varies with the reagent kit used. For example, in the size standard reagent shown in FIG. 12A as an example, known DNA fragments with lengths between 80 bp and 480 bp are labeled with fluorescent dye LIZ. The size standard is added to the samples in all the capillaries for the purpose of obtaining the relation between the scanning time and the DNA fragment length in the size calling process described below.

The operator specifies the kind of allelic ladder, the kind of size standard, the kinds of fluorescent reagent, the kinds of sample set in the respective capillaries (in the wells of the sample plate 524 corresponding to the respective capillaries) and the like. In this Example, the kind of one of the actual sample, the positive control, the negative control and the allelic ladder is specified as a kind of sample. The information is set in the sample information setting unit 106 on the data analyzer 112 through the user interface unit 103.

Step 702: Then, after the completion of the sample preparation (the step 701), the operator operates the user interface unit 103 on the data analyzer 112 shown in FIG. 1 and thus instructs to start the analysis. The instruction for the start of the analysis is passed to the electrophoresis apparatus control unit 108. The electrophoresis apparatus control unit 108 sends a signal for starting the analysis to the electrophoresis apparatus. 105, and the analysis is thus started.

Step 703: Next, filling of the migration medium (the step 703) is started in the electrophoresis apparatus 105 shown in FIG. 1. This step may be conducted automatically after the start of the analysis or conducted serially by sending a control signal from the electrophoresis apparatus control unit 108. The filling of the migration medium is a procedure of filling the capillaries 502 with a fresh migration medium to form migration paths.

In the process of filling the migration medium (the step 703) in Example 1, the waste fluid vessel 523 is first moved to right under the load header 529 with the carrier 525 shown in FIG. 1, so that the waste fluid vessel 523 can receive the used migration medium which is discharged from the capillary cathode ends 527. Then, the syringe 503 is driven to fill the capillaries 502 with a fresh migration medium and discard the used migration medium. Finally, the capillary cathode ends 527 are dipped into the washing solution in the washing vessel 522 to wash the capillary cathode ends 527 polluted by the migration medium.

Step 704: Next, preliminary electrophoresis (the step 704) is performed. This step may be conducted automatically or conducted serially by sending a control signal from the electrophoresis apparatus control unit 108. The preliminary electrophoresis is a procedure of applying a certain level of voltage to the migration medium to make the migration medium suitable for electrophoresis. In the preliminary electrophoresis process (the step 704) in this Example, the capillary cathode ends 527 are first dipped into the buffer solution in the buffer vessel 521 with the carrier 525 to form current paths. Then, voltage of about several to several dozen kilo volts is applied to the migration medium with the high voltage power supply 504 for several to several dozen minutes to make the migration medium suitable for electrophoresis. Finally, the capillary cathode ends 527 are dipped into the washing solution in the washing vessel 522 to wash the capillary cathode ends 527 polluted by the buffer solution.

Step 705: Next, sample injection (the step 705) is performed. This step may be conducted automatically or conducted serially by sending a control signal from the electrophoresis apparatus control unit 108. In the sample injection process (the step 705), the sample components are injected into the migration paths. In the sample injection process (the step 705) in this Example, the capillary cathode ends 527 are first dipped into the samples contained in the wells of the sample plate 524 with the carrier 525. This forms current paths, which enable the injection of the sample components to the migration paths. Then, pulse voltage is applied to the current paths with the high voltage power supply 504 to inject the sample components into the migration paths. Finally, the capillary cathode ends 527 are dipped into the washing solution in the washing vessel 522 to wash the capillary cathode ends 527 polluted by the samples.

Figure 2:
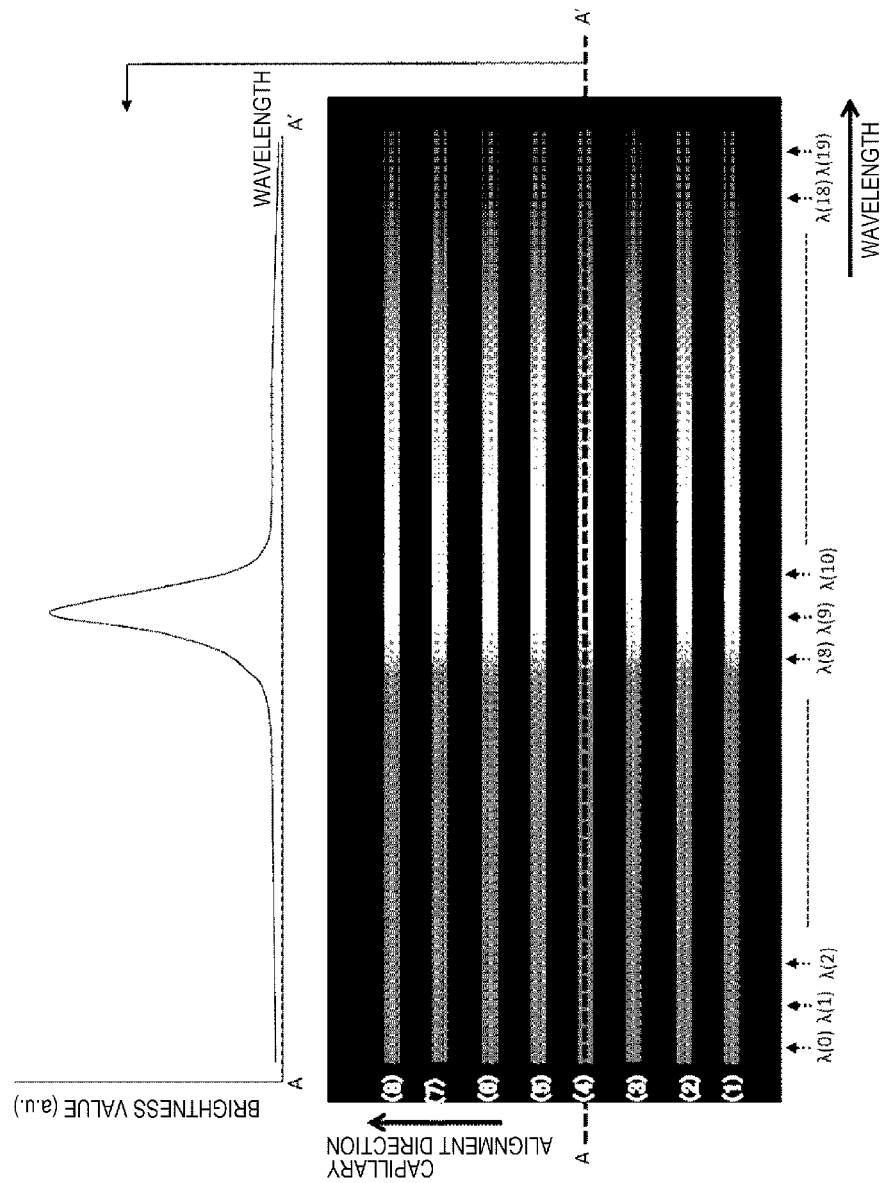
[FIG. 2] A figure showing an example of images formed on the optical detector of the electrophoresis apparatus according to Example 1.
Figure 3:
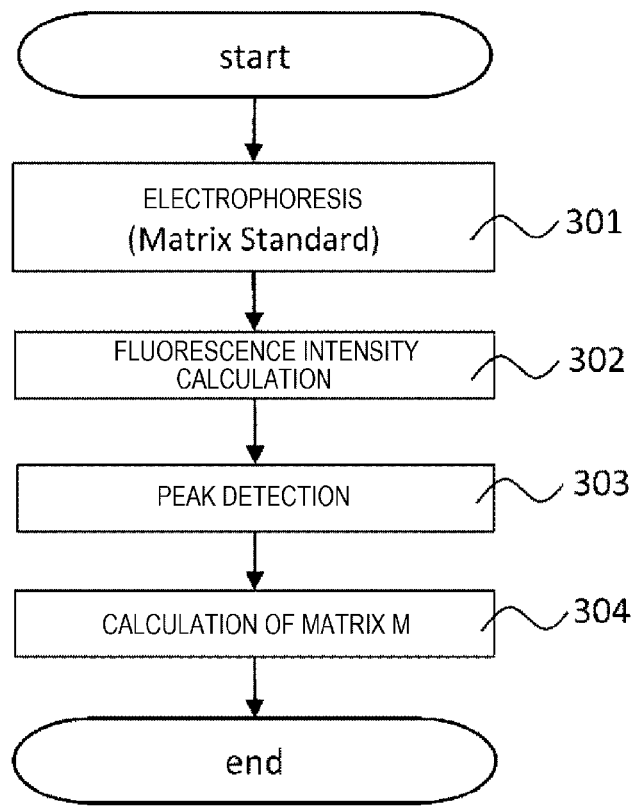
[FIG. 3] A flowchart of the spectral calibration process according to the conventional technology.
Figure 4A:
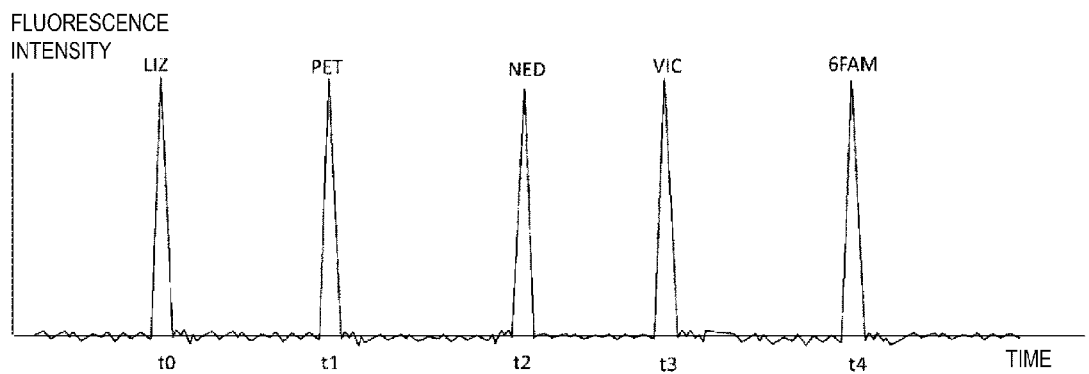
[FIG. 4A] A figure for explaining a summary of the spectral calibration according to the conventional technology.
Figure 4B:
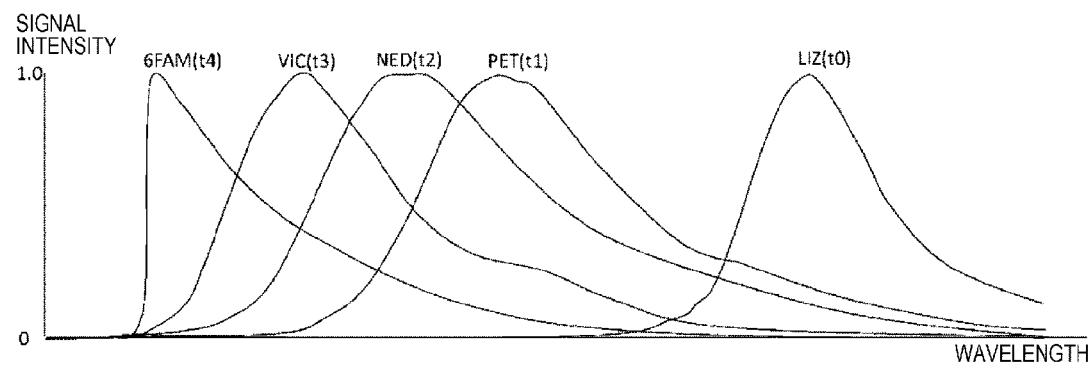
[FIG. 4B] A figure for explaining a summary of the spectral calibration according to the conventional technology.

Step 706: Next, electrophoresis analysis (the step 706) is performed. This step may be conducted automatically or conducted serially by sending a control signal from the electrophoresis apparatus control unit 108. In the electrophoresis analysis process (the step 706), the sample components contained in the samples are separated by electrophoresis and analyzed. In the electrophoresis analysis process (the step 706) in this Example, the capillary cathode ends 527 are first dipped in the buffer solution in the buffer vessel 521 with the carrier 525 to form current paths. Next, high voltage of around 15 kV is applied to the current paths with the high voltage power supply 504 to generate an electric field through the migration paths. Due to the generated electric field, the sample components in the migration paths travel towards the detection unit 516 at speeds depending on the properties of the respective sample components. That is, the sample components are separated by the differences in the migration speed. The sample components are detected in the order of arrival at the detection unit 516. For example, when a sample contains a lot of DNA fragments with different nucleotide lengths, differences in the migration speed are caused by the nucleotide lengths, and the DNA fragments reach the detection unit 516 in the order of the nucleotide length. A fluorescent dye depending on the nucleotide sequence at the end is attached to each DNA fragment. When the detection unit 516 is irradiated with excitation light from the light source 514, information light (fluorescence having a wavelength depending on the sample) is generated from a sample and emitted. The information light is detected with the optical detector 515. An example of images detected with the optical detector 515 is shown in FIG. 2. The information light is detected at a certain time interval with the optical detector 515 during the electrophoresis analysis, and the image data are sent to the data analyzer 112. Alternatively, brightness degrees of a region of the image data may be sent, instead of the image data, to reduce the information amount to be sent. For example, brightness values at wavelengths at a certain interval of each capillary may be sent.

Figure 8:
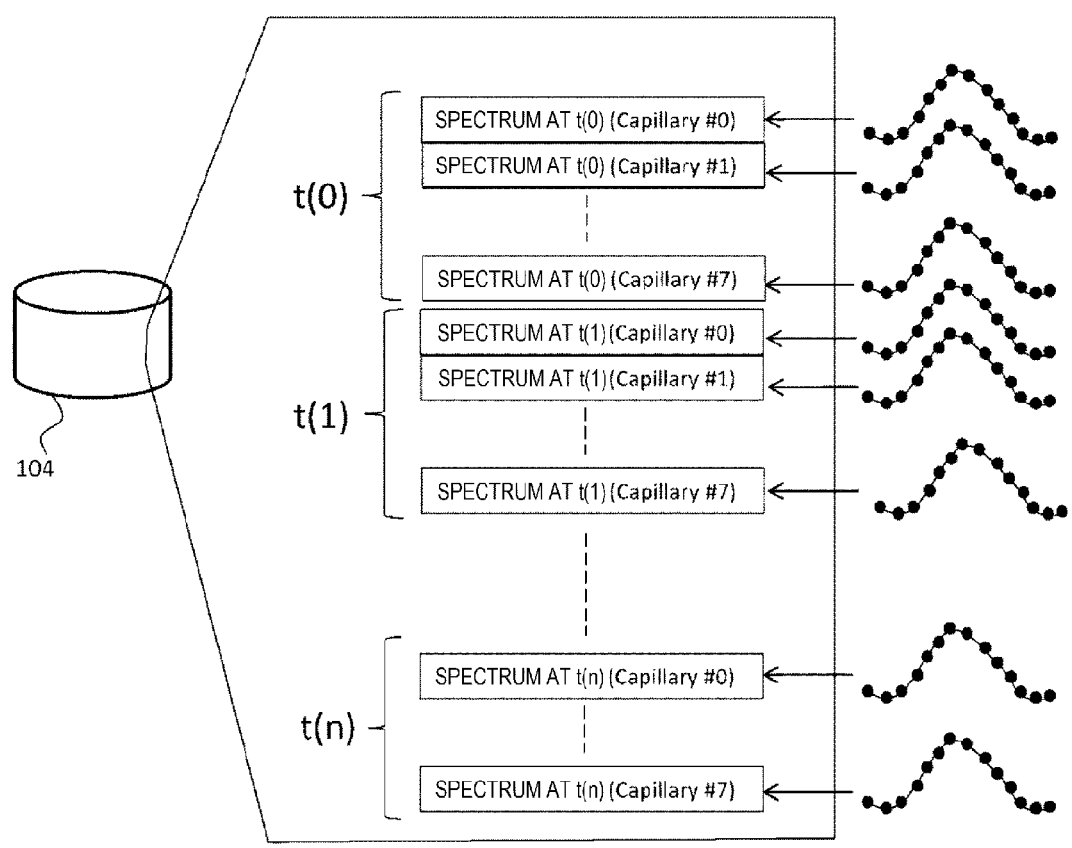
[FIG. 8] A figure showing an example of storage of spectral data according to Example 1.

In this Example, it is supposed that, from the image data, only the brightness value data at 20 wavelengths ($\lambda(0)$ to $\lambda(19)$) of each capillary are sent to the data analyzer 112, as described in the explanation of FIG. 2. The brightness value data contain the spectra of the capillaries. The spectra are stored in the storage unit 104 (see FIG. 8). As shown in FIG. 8, the spectra of all the capillaries at all the detection times during the electrophoresis analysis are stored in the storage unit 104. In this regard, although it is desirable that the spectra at all the detection times are stored in this Example, only the spectrum at around a specific peak time may be stored when only the specific peak time is important for STR analysis.

Step 707: Finally, the application of the voltage is stopped after obtaining the planned image data to complete the electrophoresis analysis (a step 707).

The above processes are example processes of the electrophoresis process (the step 601) of FIG. 6.

<Explanation of the Step 602>

Next, an example of the process of calculating of the fluorescent dye intensities in FIG. 6 is explained.

From the image data obtained in the electrophoresis process (the step 601), the intensities of the respective fluorescent dyes are calculated (the step 602). The fluorescence intensity calculation process is conducted in the fluorescence intensity calculation unit 110 shown in FIG. 1. In the fluorescence intensity calculation process (the step 602), the spectra of a capillary at the respective times should be multiplied by the intensity ratios of the respective fluorescent dyes at the respective wavelengths $\lambda(0)$ to $\lambda(19)$ and summed. A matrix representing this is shown by (Formula 1).

Here, the vector C is a fluorescence intensity vector, and the elements $C_F$, $C_V$, $C_N$, $C_P$ and $C_L$ are the fluorescence intensities of 6FAM, VIC, NED, PET and LIZ, respectively.

Figure 28:
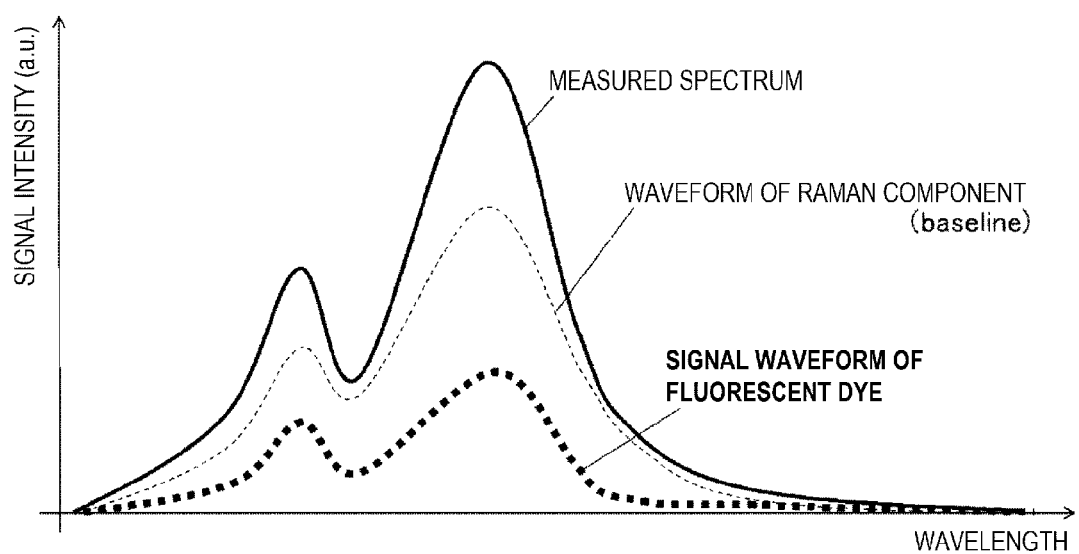
[FIG. 28] A figure for explaining the concept of a baseline signal of a measured spectrum according to Example 1.

The vector f is a measured spectrum vector, and the elements $f_0$ to $f_{19}$ are the signal intensities (brightness values) at the wavelengths $\lambda(0)$ to $\lambda(19)$, respectively. Alternatively, the elements $f_0$ to $f_{19}$ may be the averages of the signal intensities near the wavelengths $\lambda(0)$ to $\lambda(19)$, respectively. In this regard, the measured signal at each of the wavelengths $\lambda(0)$ to $\lambda(19)$ detected with the optical detector 515 contains Raman-scattered light from the polymer filling the capillary as a baseline signal, in addition to the signal from a fluorescent dye. Thus, when the vector f is calculated, the baseline signal should be removed in advance (see FIG. 28).

Figure 29:
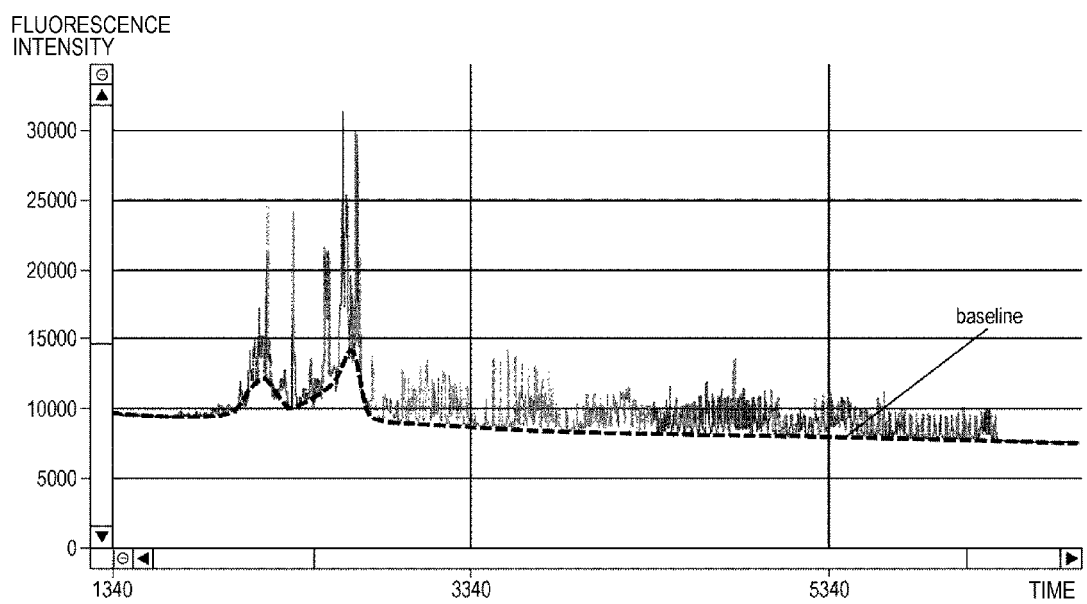
[FIG. 29] A figure for explaining the concept of a baseline signal of time series data of a measured spectrum according to Example 1.

In an example method for removing the baseline signal, the spectrum of the Raman-scattered light is measured in advance before shipping the apparatus and is stored in the storage unit 104 as the baseline signal. Then, by subtracting the baseline signal from the measured signal at a time, the signal of a fluorescent dye may be determined, and this signal may be used as the measured spectrum vector f. As shown in FIG. 29, when the measured signals at the wavelengths ($\lambda(0)$ to $\lambda(19)$) are observed as time series data, the signals from the fluorescent dyes can be intuitively distinguished from the other baseline signal. Thus, the baseline signal may be removed also by high-pass filtering of the measured signals at the wavelengths ($\lambda(0)$ to $\lambda(19)$) to remove low-frequency components. The minimum value around each time may be used as the baseline signal value at the time.

The matrix M is a matrix converting the measured spectrum f into the fluorescence intensity vector, and the elements correspond to the intensity ratios of the respective fluorescent dyes at the respective wavelengths. For example, the element $W_{F0}$ in the matrix M in Formula 1 is the ratio of the fluorescence intensity of the fluorescent dye 6FAM at the wavelength $\lambda(0)$. A higher value means that the contribution of the fluorescent dye to the intensity at the wavelength is higher.

[Math. 1]

$$c = Mf \quad \text{(Formula 1)}$$
$$c = [c_F \ c_V \ c_N \ c_P \ c_L]^t$$
$$f = [f_0 \ f_1 \ \cdots \ f_{18} \ f_{19}]^t$$
$$M = \begin{bmatrix} w_{F0} & w_{F1} & & w_{F18} & w_{F19} \\ w_{V0} & w_{V1} & & w_{V18} & w_{V19} \\ w_{N0} & w_{N1} & \cdots & w_{N18} & w_{N19} \\ w_{P0} & w_{P1} & & w_{P18} & w_{P19} \\ w_{L0} & w_{L1} & & w_{L18} & w_{L19} \end{bmatrix}$$

Originally, the matrix M is determined exclusively by the kinds of fluorescent dye and the conditions of the migration path, but in practice, the matrix M may change depending on the positional relation between the capillary and the detector and must be thus calculated when the capillary is changed or the like. The series of processes for determining the matrix M is spectral calibration.

In this Example, it is supposed that the initial value of the matrix is obtained in advance through measurement. It is also supposed that the fluorescence spectra for obtaining the initial matrix, which will be described below, are similarly obtained in advance. Moreover, in this Example, it is supposed that the initial matrix determined in advance through measurement and the fluorescence spectra (described below) for obtaining the initial matrix are stored in the storage unit 104 for each kind or product of fluorescent reagent for the genotype analyzer. Alternatively, the matrix obtained in the previous spectral calibration and the fluorescence spectra thereof may be stored in the storage unit 104 as the initial values. However, because the matrix can be derived from the fluorescence spectra and the fluorescence spectra can be derived from the matrix as described below, only information about either of them may be stored.

When the kinds of fluorescent reagent are set in the sample information setting unit 106 during the sample preparation (the step 701) of the electrophoresis process in FIG. 7, the initial value of the matrix corresponding to the kinds of fluorescent reagent is passed to the fluorescence intensity calculation unit 110.

When the matrix obtained in the previous spectral calibration is stored in the storage unit 104 and the kinds of fluorescent reagent are same as the kinds of fluorescent reagent used this time, the previous matrix may be used as the initial value.

Using the initial value of the matrix M, the fluorescence intensities of the respective fluorescent dyes are calculated from measured spectra according to (Formula 1). By processing the spectra of a capillary at the respective times in the manner, time series data of the fluorescence intensities of the capillary can be obtained. The time series data of the fluorescence intensities are referred to as fluorescence intensity waveforms below.

Figure 9:
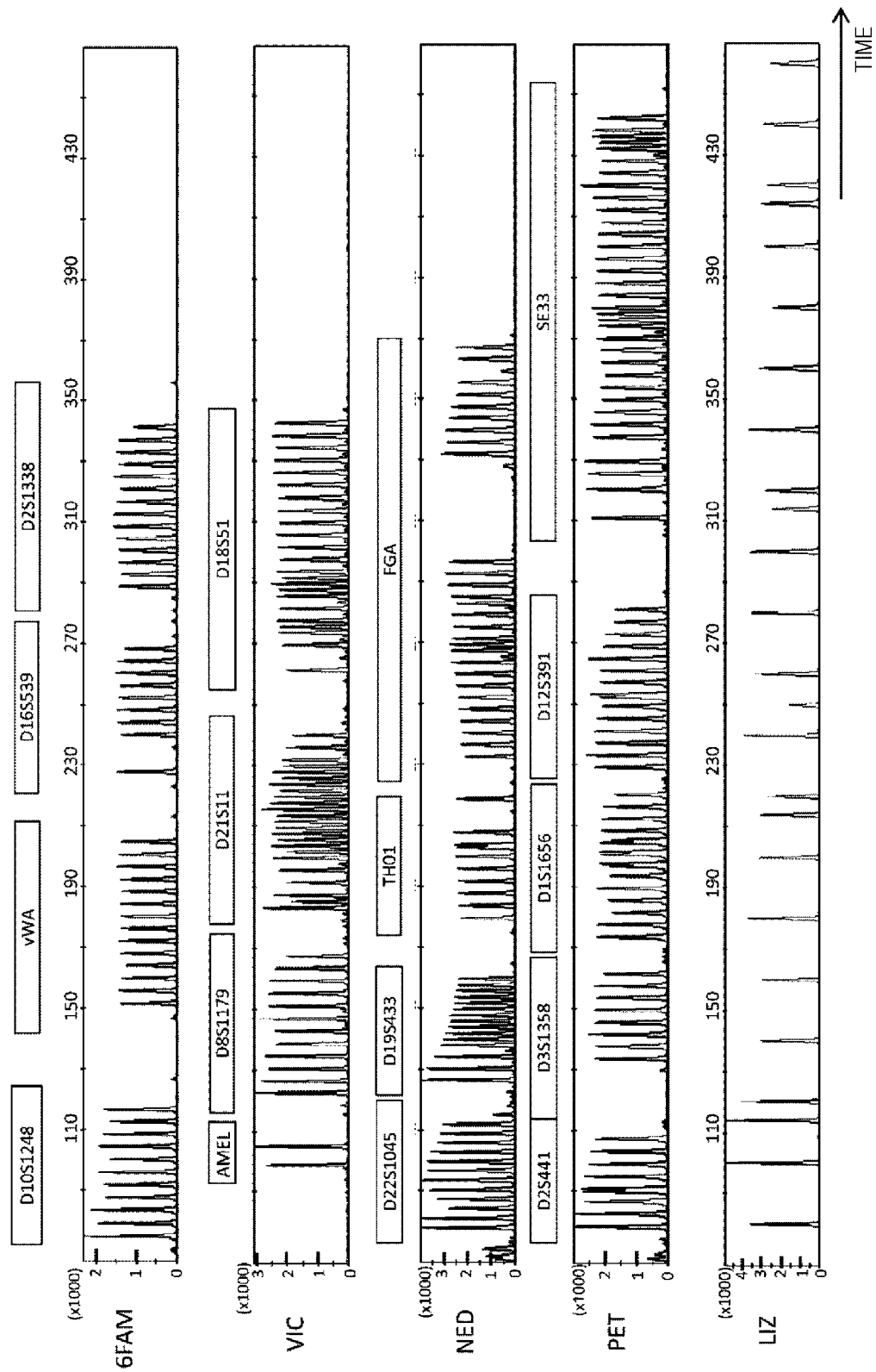
[FIG. 9] A figure showing an example of fluorescence intensity waveforms of an allelic ladder.
Figure 10:
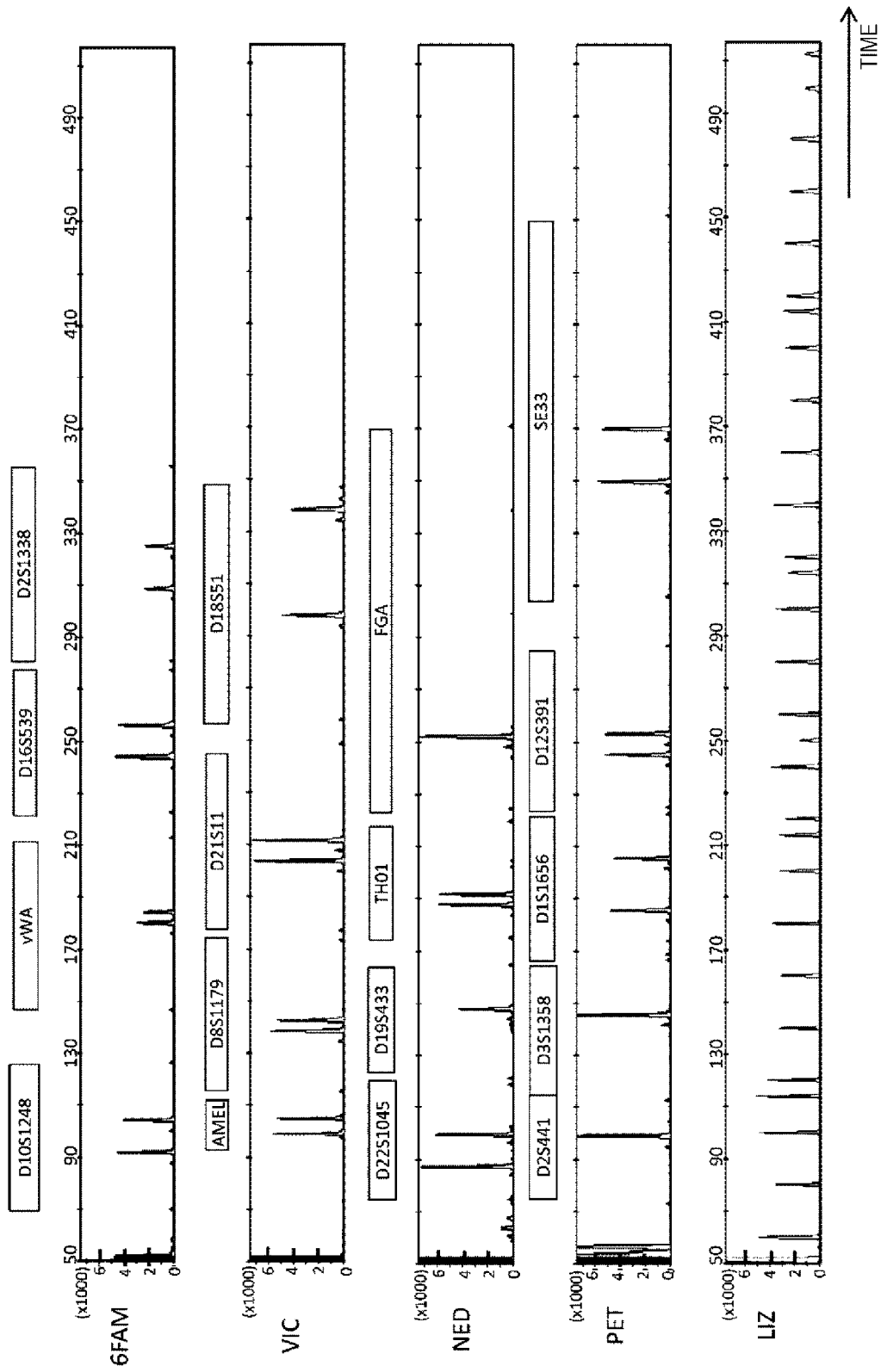
[FIG. 10] A figure showing an example of fluorescence intensity waveforms of an actual sample.

Examples of the change in the fluorescence intensity with time obtained in the step 602 after electrophoresis (the step 601) are shown in FIG. 9 and FIG. 10. FIG. 9 shows example fluorescence intensity waveforms obtained by electrophoresis of an allelic ladder. FIG. 10 shows example fluorescence intensity waveforms of an actual sample. The time of a peak of fluorescence intensity corresponds to the length of a DNA fragment labeled with a fluorescent dye, and the difference in the length corresponds to the difference in the allele. It is seen that, since the allelic ladder is an artificial sample containing many alleles which are generally contained in DNA markers, many peaks are observed in the fluorescence intensity waveforms in FIG. 9. In the fluorescence intensity waveforms of an actual sample shown in FIG. 10, one or two peaks are observed for a DNA marker, and it is seen that when there is only one peak, the fluorescence intensity of the peak is higher than the fluorescence intensities of a marker having two peaks. A case with one peak means that the locus is homo (the paternal allele and the maternal allele are the same), while a case with two peaks means that the locus is hetero (the paternal allele and the maternal allele are different). Although FIG. 10 shows an example where one individual contributes to the sample DNA, when the sample is a mixture of DNA from two or more individuals, one DNA marker may have three or more peaks depending on the contributions of the individuals.

<Explanation of the Step 603>

Next, an example of the peak detection process in FIG. 6 is explained.

Peaks are detected (the step 603) from the fluorescence intensity waveforms obtained in the fluorescence intensity calculation process (the step 602) in FIG. 6. For the peak detection, the peak center (peak time), the peak height and the peak width are mainly important. Each peak center corresponds to the length of a DNA fragment and is most important for identifying the allele. The peak height is used for the identification of homo and hetero types and for the quality assessment such as the degree of DNA concentration of the sample. The peak width is also important for assessing the quality of the sample and the electrophoresis results. As means for estimating the peak parameters of actual data, Gaussian fitting, which is a known technique, can be used.

Figure 11:
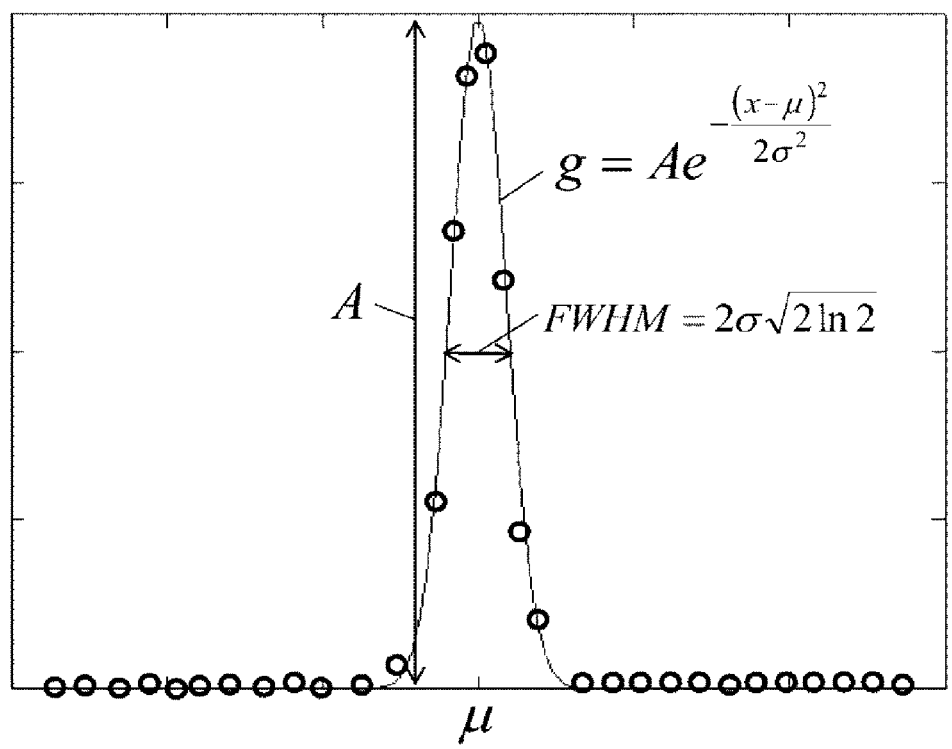
[FIG. 11] A figure for explaining a summary of Gaussian fitting.

The concept of Gaussian fitting is shown in FIG. 11. As shown in the figure, Gaussian fitting is a process of calculating parameters (mean $\mu$, standard deviation $\sigma$ and maximum amplitude A) giving a Gaussian function g which best approximates the actual data, with respect to the actual data in a certain range. The least square error of the actual data and the Gaussian function value is often used as an index for the degree of approximation of the actual data. Using conventional means such as the Gauss-Newton method as means for calculating values which minimize the least square error, the parameters can be optimized. In addition, means for improving the accuracy when two or more peak waveforms are mixed or when the data around the peak are asymmetric, as disclosed in PTL 1, may be applied. When the variance $\sigma$ of the Gaussian function g is determined, the full width at half maximum (FWHM) is obtained by the formula shown in FIG. 11. This value can be used as the peak width.

The peak parameters are determined for all of the fluorescence intensity waveforms of the fluorescent dyes in this manner. Here, when a peak width or a peak height does not meet the threshold condition which is determined in advance, the peak may be excluded.

<Explanation of the Step 604>

Next, an example of the size calling process in FIG. 6 is explained.

Size calling is a process of matching the period required for detecting a DNA fragment by electrophoresis to the DNA fragment length, and in this Example, size calling is performed by the STR analysis unit 111 in the data analyzer 112. Specifically, as described above, a reagent containing DNA fragments which have known lengths and are labeled with a specific fluorescent dye (here, the reagent is called a size standard) is subjected to electrophoresis. For example, with respect to the size standard reagent shown in FIG. 12A as an example, known DNA fragments with lengths between 80 bp and 480 bp are labeled with fluorescent dye LIZ. The centers of the peaks (namely, the peak times) obtained in the peak detection (the step 603) are matched to the known DNA fragment lengths. The relational expression of the electrophoresis time and the DNA fragment length can be derived from the combinations of the peak time and the known DNA fragment length.

Figure 12B:
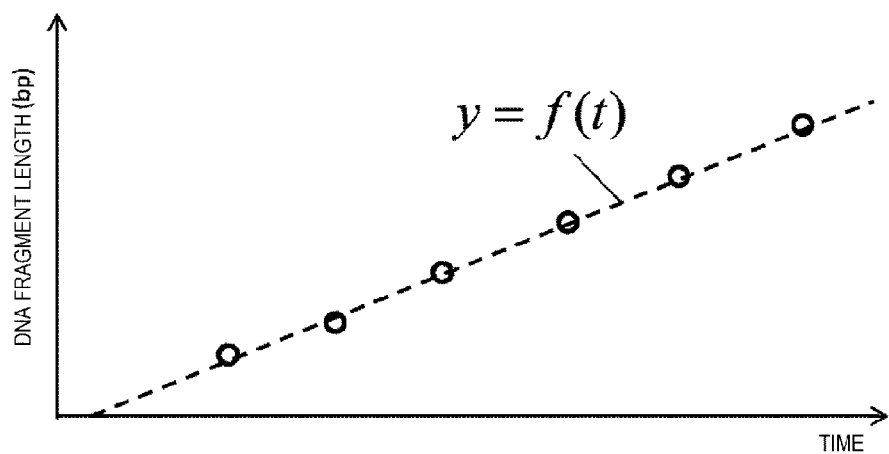
[FIG. 12B] A figure for explaining a summary of size calling according to Example 1.

FIG. 12B is a figure showing the process of determining the relational expression of the DNA migration time (t) and the DNA fragment length (y) "y=f(t)". The known DNA fragment lengths of the size standard are plotted against the peak times, and a relational expression y=f(t) which best approximates the plot is determined. The expression f(t) may be approximated using a quadratic equation, a cubic equation or the like in such a manner that the square error becomes the smallest. The user may specify an approximate equation to be used for the STR analysis unit 111 through the user interface unit 103. Thus derived relational expression of the DNA migration time (t) and the DNA fragment length (y) "y=f(t)" is determined for every capillary and stored. A DNA fragment length can be determined using the relational expression from a peak time of a fluorescence intensity waveform measured in a capillary.

<Explanation of the Step 605>

Next, an example of the process of obtaining the reference fluorescence spectra in FIG. 6 is explained.

The reference fluorescence spectra are fluorescence spectra serving as standards to determine the fluorescence spectra of another capillary by shifting the reference fluorescence spectra. In this specification, the capillary in which electrophoresis of the allelic ladder is carried out is called the reference capillary, and the fluorescence spectra of the reference capillary are called the reference fluorescence spectra. In this Example, this process is conducted by the matrix calculation unit 109 of the data analyzer 112 in FIG. 1.

When the acquisition fails in the reference fluorescence spectrum process, the initial fluorescence spectra of the reference capillary (on the supposition that the initial fluorescence spectra are stored in the storage unit 104) may be used as the reference fluorescence spectra. Alternatively, STR analysis may be conducted using the fluorescence intensity waveforms to which the initial matrix is applied through the path 610.

Figure 13:
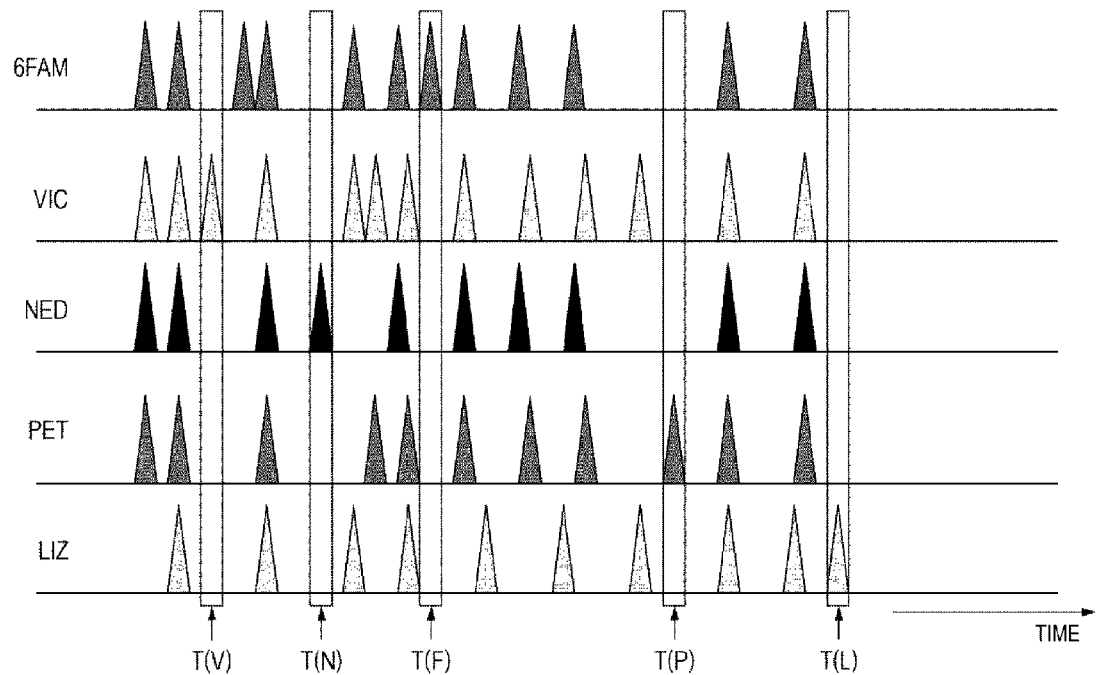
[FIG. 13] A figure for explaining a summary of acquisition of reference fluorescence spectra according to Example 1.
Figure 14:
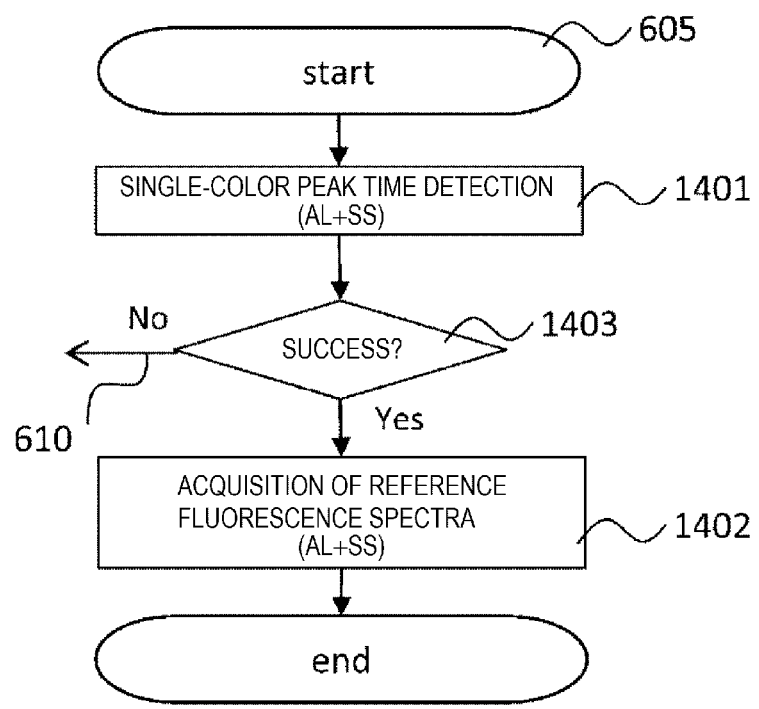
[FIG. 14] A flowchart of the acquisition process of reference fluorescence spectra according to Example 1.

The acquisition process of the reference fluorescence spectra (the step 605) is explained using FIG. 13 and FIG. 14. FIG. 13 is a schematic diagram of the fluorescence intensity waveforms of the fluorescent dyes of the reference capillary, in other words, the waveforms shown in FIG. 9. The figure shows the fluorescence intensity waveforms of the allelic ladder and the size standard, where the allelic ladder is labeled with 6FAM, VIC, NED and PET and the size standard is labeled with LIZ.

FIG. 14 is a flowchart of the acquisition process of the reference fluorescence spectra (the step 605).

As shown in the figure, in this Example, a time at which a peak of only one fluorescent dye is observed (referred to as a single-color peak time below) is extracted from the five fluorescence intensity waveforms of the reference capillary (a step 1401). The spectrum at the single-color peak time is obtained (a step 1402) and used as the fluorescence spectrum of the color.

The detection process of the single-color peak times in the step 1401 is explained below.

In FIG. 13, T(V), T(N), T(F), T(P) and T(L) are the single-color peak times of fluorescent dyes VIC, NED, 6FAM, PET and LIZ, respectively, and it is supposed that the other fluorescent dyes do not contribute to the fluorescence intensity at a time.

The single-color peak times can be determined depending on the kinds of allelic ladder and size standard set in the electrophoresis apparatus. In other words, information about the DNA fragment lengths contained in the reagent is always disclosed for the allelic ladder and the size standard, and the information is used for STR analysis, which will be described below. The known DNA fragment lengths of the size standard are used for obtaining the relational expression of the electrophoresis time and the DNA fragment length in the size calling process, as already described. The fluorescence intensity waveforms of the allelic ladder are as shown in FIG. 9, and the peaks observed in the figure correspond to the lengths of the DNA fragments contained in the allelic ladder. A part of the information concerning the DNA fragments contained in the allelic ladder is shown in FIG. 15.

In the figure, names of loci (Locus) labeled with fluorescent dyes (Dye), names of alleles contained in the loci (Allele), the DNA fragment lengths corresponding to the alleles (Length) and acceptable widths of the nucleotide length from the centers of the alleles (Min/Max) are shown as the information about the allelic ladder. For example, in the figure, DNA marker (locus) D10S1248 is labeled with 6FAM and contains alleles 8, 9, 10, 11, 12, 13, 14, 15, 16, 17 and 18, and their DNA fragment lengths (unit is bp) are 77, 81, 85, 89, 93, 97, 101, 109, 113 and 117, respectively. It is shown that all of the alleles have an acceptable width of +0.5 bp to −0.5 bp. Each of the alleles corresponds to one peak in the fluorescence intensity waveforms. Although only an example of the information about DNA marker D10S1248 is shown in FIG. 15, similar information is disclosed for all the loci contained in the allelic ladder. Such information about the DNA fragment lengths of the allelic ladder is stored in the storage unit 104 in advance, and when the kind of allelic ladder is set during the sample preparation (the step 701 in FIG. 7), the information about the DNA fragment lengths of the set kind of allelic ladder in the storage unit 104 may be read by the matrix calculation unit 109. Accordingly, because the DNA fragment lengths are known for all of the peaks in the fluorescence intensity waveforms of the allelic ladder shown in FIG. 9, the single-color peak times may be extracted using the known information.

Figure 16:
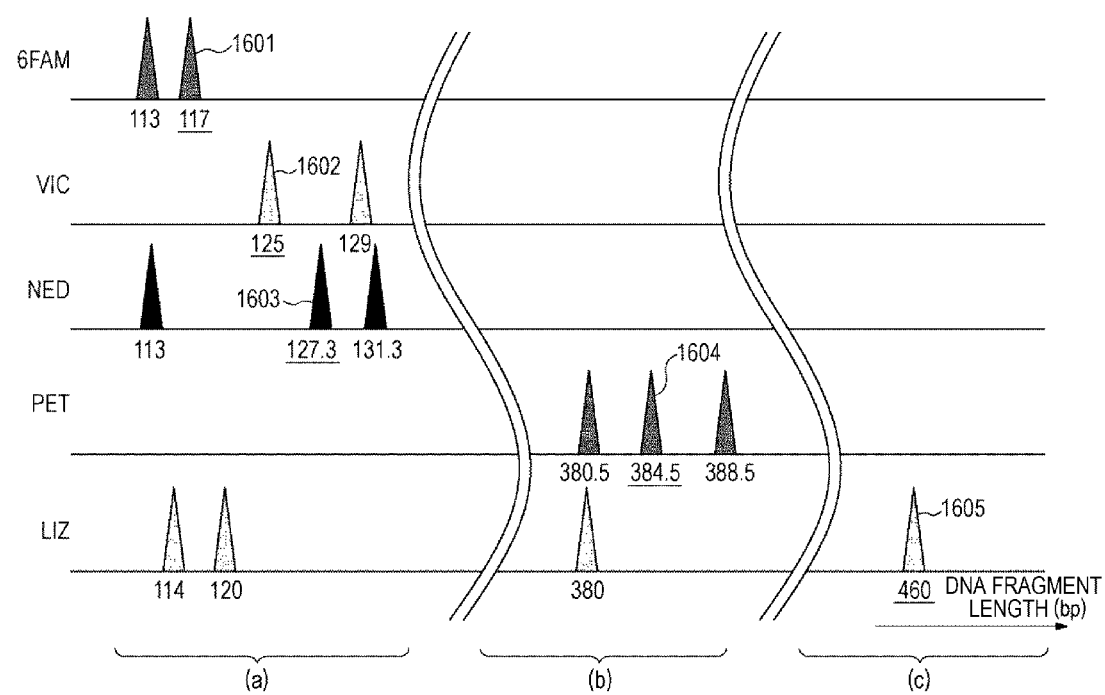
[FIG. 16] A figure for explaining an example of extraction of single-color peak times according to Example 1.

An example for extracting the single-color peak times using the information concerning the DNA fragment lengths attached to the allelic ladder is shown in FIG. 16. In the figure, peak positions of the fluorescence intensity waveforms are shown. In this regard, although the horizontal axis corresponds to the DNA fragment length instead of the electrophoresis time in the figure, both are essentially the same because there is a one-to-one correspondence between them through size calling. All of the peaks of the fluorescent dyes for the DNA fragment lengths between 113 bp and 130 bp are aligned and shown in (a) of the figure. The maximum acceptable width of each peak is ±0.5 bp from the peak center. From the positional relation of the peaks in (a) of the figure, it is seen that a peak 1601 (DNA fragment length of 117 bp) for 6FAM, a peak 1602 (DNA fragment length of 125 bp) for VIC and a peak 1603 (DNA fragment length of 127.3 bp) for NED can be extracted as the single-color peak times of the respective fluorescent dyes. Similarly, all of the peaks of the fluorescent dyes around 380 bp are aligned and shown in (b) of the figure. From the figure, it is seen that a peak 1604 (DNA fragment length of 384.5 bp) can be extracted as the single-color peak time for PET. Similarly, all of the peaks of the fluorescent dyes around 460 bp are shown in (c) of the figure. From the figure, it is seen that a peak 1605 (DNA fragment length of 460 bp) can be extracted as the single-color peak time for fluorescent dye LIZ.

When the single-color peak times are not obtained, STR analysis may be conducted using the fluorescence intensity waveforms to which the initial matrix is applied through the path 610.

Next, the acquisition process of the reference fluorescence spectra (the step 1402) in FIG. 14 is described.

As already described in the explanation of FIG. 8, the spectra of all the capillaries at all the detection times are stored in the storage unit 104 in this Example. Accordingly, in the step 1401, based on the information about the known DNA fragment lengths of the allelic ladder and the size standard, the single-color peak times of the reference capillary are extracted, and the spectra at the times are obtained from the storage unit 104. The spectra are used as the reference fluorescence spectra. The acquisition process of the reference fluorescence spectra (the step 605) in FIG. 6 is conducted in such a manner.

<Explanation of the Step 606>

Next, an example of the fluorescence spectrum calculation process in FIG. 6 is explained.

This process is a process of determining the fluorescence spectra of a capillary other than the reference capillary based on the reference fluorescence spectra obtained in the step 605. In this Example, this process is conducted using the fluorescence spectra of the size standard, which is subjected to electrophoresis in all the capillaries.

Figure 17:
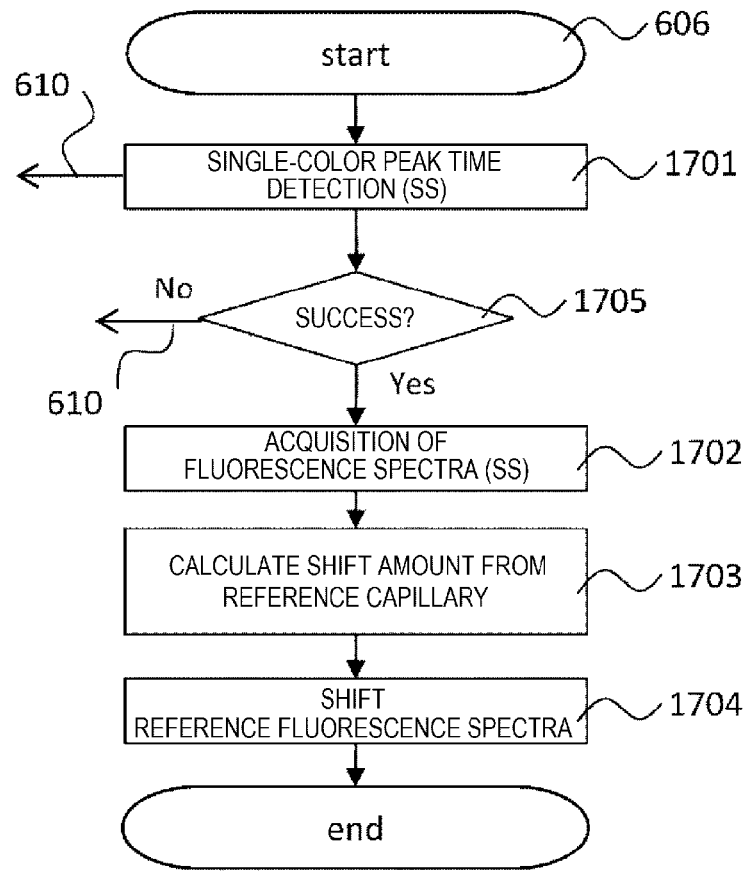
[FIG. 17] A flowchart of the fluorescence spectrum calculation process according to Example 1.

The flow of the fluorescence spectrum calculation process (the step 606) is shown in FIG. 17. In this Example, the fluorescence spectrum calculation process (the step 606) is carried out for a capillary other than the reference capillary. First, a single-color peak time of the size standard is detected (a step 1701). Example fluorescence intensity waveforms of an actual sample have already been described in the explanation of FIG. 10. Many peak values corresponding to the known DNA fragment lengths are observed in the fluorescence intensity waveform of fluorescent dye LIZ shown in FIG. 10, and all the peak times of the fluorescence intensity waveforms have already been detected in the step 603. A single-color peak time of fluorescent dye LIZ is extracted using the peak time information. That is, as in the single-color peak time detection (the step 1401) in FIG. 14, a time at which only fluorescent dye LIZ has a peak should be found. In general, the size standard often contains a DNA fragment with a length larger than the maximum value expected for electrophoresis of an actual sample, and the peak corresponding to the largest DNA fragment length may be used for the single-color peak time. For example, the peak 1605 (DNA fragment length of 460 bp) is the largest DNA fragment length in the example shown in FIG. 16. When there is no single-color peak time for LIZ in the step 1701 due to the influence of noise and the like, STR analysis may be conducted by applying the initial matrix for the capillary through the path 610 in FIG. 6.

Next, the fluorescence spectrum of LIZ at the single-color peak time of LIZ is obtained (a step 1702). As in the acquisition process of the reference fluorescence spectra (the step 1402) in FIG. 14, in this process, the spectrum at the single-color peak time of LIZ should be obtained from the spectra of all the capillaries at all the times stored in the storage unit 104. The spectrum is the fluorescence spectrum of LIZ.

Next, a shift amount of the fluorescence spectra of a capillary other than the reference capillary (referred to as the other capillary below) from the reference fluorescence spectra is calculated (a step 1703). The fluorescence spectra of the fluorescent dye labeling the size standard (LIZ in this Example) are used for calculating the shift amount. The calculation of the shift amount is explained below using FIG. 18 and FIGS. 19A and B.

Figure 18:
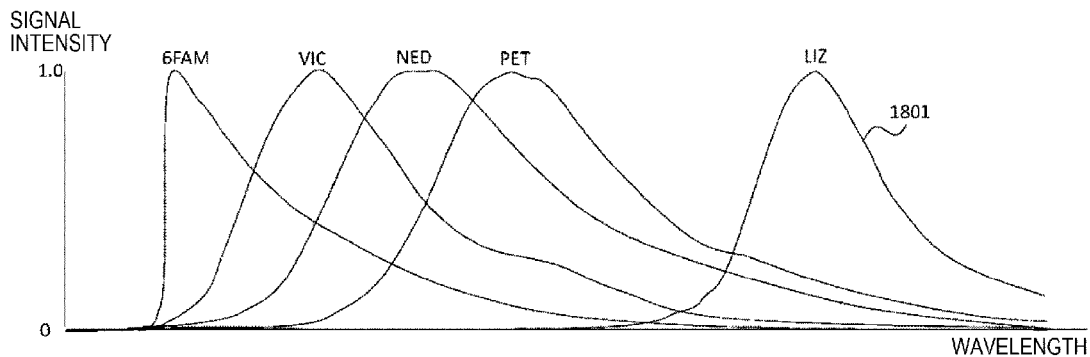
[FIG. 18] A figure showing an example of reference fluorescence spectra according to Example 1.

FIG. 18 shows an example of the reference fluorescence spectra. In the figure, the peak heights of the fluorescence spectra of all the fluorescent dyes are normalized. When a sampling interval of the fluorescence spectrum data is large as compared to the shift amount described below, the sampling interval is made small enough relative to the fluorescence spectra in advance through known spline interpolation and the like. Similarly, the data are interpolated in such a manner that the sampling interval becomes the same also for the fluorescence spectrum waveform of LIZ in the other capillary.

Figure 19A:
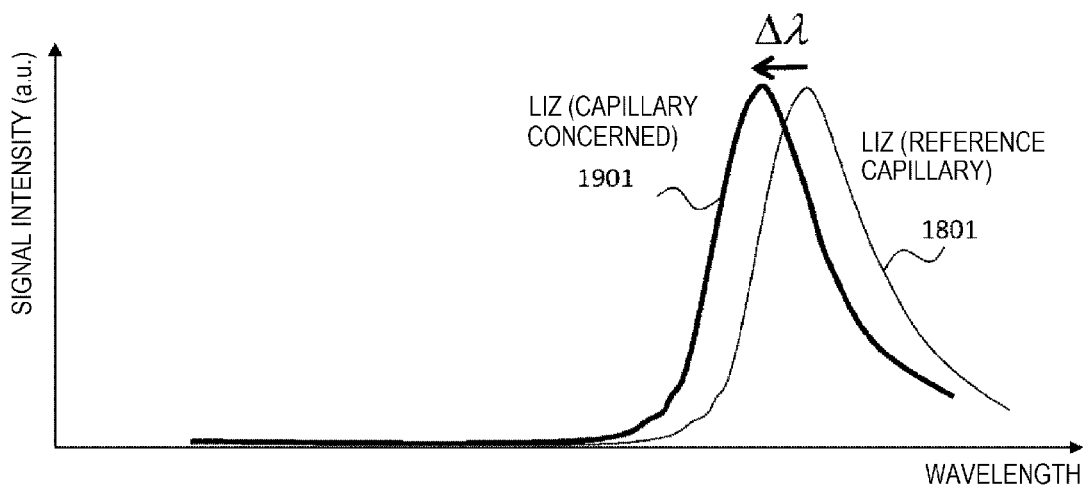
[FIG. 19A] A figure for explaining a summary of fluorescence spectrum calculation according to Example 1.

The shift amount $\Delta\lambda$ between a fluorescence spectrum 1801 of LIZ among the reference fluorescence spectra and a fluorescence spectrum 1901 in the other capillary is calculated (see FIG. 19A). To calculate the shift amount, for example, a cross-correlation function $h(m)=\Sigma f(n)*g(m-n)$, where f(n) represents the fluorescence spectrum 1801 (the interpolated waveform) and g(n) represents the fluorescence spectrum 1901 (the interpolated waveform), may be calculated, and a shift amount m at which the value becomes the maximum may be determined and used as $\Delta\lambda$. Alternatively, the peak wavelengths of the fluorescence spectrum 1801 and the fluorescence spectrum 1901 may be determined by Gaussian fitting described above, and the difference between the peak wavelengths may be used as the shift amount $\Delta\lambda$.

Figure 19B:
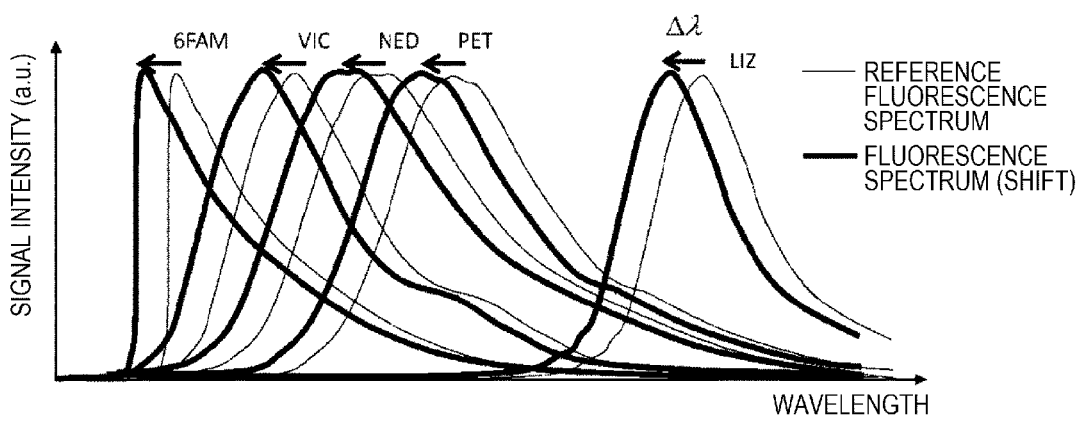
[FIG. 19B] A figure for explaining a summary of fluorescence spectrum calculation according to Example 1.

Next, all the reference fluorescence spectra of the fluorescent dyes are shifted by $\Delta\lambda$ to determine the fluorescence spectra of the other capillary (the step 1704 in FIG. 17). As shown in FIG. 19B, all the reference fluorescence spectra of the fluorescent dyes obtained in FIG. 18 should be shifted by $\Delta\lambda$ in this process. Then, the values of the waveforms at the sampling wavelengths before the interpolation ($\lambda(0)$ to $\lambda(19)$ in this Example) should be newly calculated from the interpolated fluorescence spectra.

The fluorescence spectra of the other capillary are obtained in the above manner. Such a process is conducted for all of the capillaries other than the reference capillary to determine the fluorescence spectra of the capillaries.

<Explanation of the Step 607>

Next, an example of the process for calculating the matrix in FIG. 6 is explained.

In the flow shown in FIG. 6, the matrix M is calculated using the fluorescence spectra of a capillary obtained in the step 606 (the step 607). In this Example, this process is conducted by the matrix calculation unit 109.

Although an Example of the matrix calculation process for one capillary is described below, a similar process can be applied to the other capillaries.

With respect to a capillary, the fluorescence spectra of the five kinds of fluorescent dye, namely 6FAM, VIC, NED, PET and LIZ, obtained in the step 606 are represented by vectors $S_F$, $S_V$, $S_N$, $S_P$ and $S_L$, respectively. Here, the number of dimensions of the vectors $S_F$, $S_V$, $S_N$, $S_P$ and $S_L$ is 20. In other words, as described above, the elements of each vector are the signal intensities of the respective fluorescence spectra at the wavelengths $\lambda(0)$ to $\lambda(19)$. Moreover, a spectrum measured at a certain time is represented by a vector f, and the fluorescence intensity vector thereof is represented by C. The vector f and the vector C are similar to those in (Formula 1). That is, the elements $C_F$, $C_V$, $C_N$, $C_P$ and $C_L$, of the vector C indicate the fluorescence intensities of 6FAM, VIC, NED, PET and LIZ, respectively. The elements $f_0$ to $f_{19}$ of the vector f indicate the signal intensities (brightness values) at the wavelengths $\lambda(0)$ to $\lambda(19)$, respectively.

Here, when a matrix S containing the fluorescence spectrum vectors $S_F$, $S_V$, $S_N$, $S_P$ and $S_L$ as columns is referred to as a fluorescence spectrum matrix, the relational expression of (Formula 2) is derived. By comparing (Formula 1) and (Formula 2), it is seen that the matrix M corresponds to the inverse of the fluorescence spectrum matrix S. However, since the fluorescence spectrum matrix S is a non-square matrix (20×5 in (Formula 2)), the inverse thereof cannot be derived in this form. This corresponds to a situation that the conditions are excessive because the number of conditional equations is 20 while the number of unknown quantities is 5 ($C_F$, $C_V$, $C_N$, $C_P$ and $C_L$) and thus the unknown quantities satisfying all the conditional equations cannot be obtained.

Thus, it is known that the matrix M can be derived from a matrix $(S^tS)^{-1}S^t$ shown in (Formula 3), not from the inverse of the fluorescence spectrum matrix S. The matrix $(S^tS)^{-1}S^t$ is called a pseudoinverse matrix. Because the point that (Formula 3) is equivalent to the calculation of the five unknown quantities ($C_F$, $C_V$, $C_N$, $C_P$ and $C_L$) by the least square method is derived, the pseudoinverse matrix $(S^tS)^{-1}S^t$ is also called a least-square-type generalized inverse matrix.

[Math. 2]

$$f = Sc \quad \text{(Formula 2)}$$
$$c = [c_F \ c_V \ c_N \ c_P \ c_L]^t$$
$$f = [f_0 \ f_1 \ \cdots \ f_{18} \ f_{19}]^t$$
$$S = [s_F \ s_V \ s_N \ s_P \ s_L] = \begin{bmatrix} s_{F0} & s_{V0} & s_{N0} & s_{P0} & s_{L0} \\ s_{F1} & s_{V1} & s_{N1} & s_{P1} & s_{L1} \\ \vdots & \vdots & \vdots & \vdots & \vdots \\ s_{F18} & s_{V18} & s_{N18} & s_{P18} & s_{L18} \\ s_{F19} & s_{V19} & s_{N19} & s_{P19} & s_{L19} \end{bmatrix}$$

[Math. 3]

$$M = (S^tS)^{-1}S^t \quad \text{(Formula 3)}$$

[Math. 4]

$$S = (M^tM)^{-1}m^t \quad \text{(Formula 4)}$$

Accordingly, in the matrix calculation process of the step 607, the matrix M can be obtained by calculating the pseudoinverse matrix of (Formula 3) of the fluorescence spectrum matrix S obtained from the fluorescence spectra obtained in the step 606. Such matrices are determined for all the capillaries and stored.

In this regard, because (Formula 4) is derived from the relation of (Formula 1) and (Formula 2) like (Formula 3), the information concerning the fluorescence spectra can easily be calculated from the matrix information.

In the matrix calculation process in the step 607, the reliability of the matrix M is evaluated, and when the reliability is determined to be low, STR analysis may be conducted using the fluorescence intensity waveforms to which the initial matrix is applied through the path 610 in FIG. 6 without using the matrix M. An example of the index for the reliability of the matrix M is the condition number of the matrix derived from the product of the transpose of the fluorescence spectrum matrix S shown in (Formula 2) multiplied by the matrix S. The condition number of a matrix is represented by the product of the norm of the matrix multiplied by the norm of its inverse. The equation is shown by (Formula 5).

[Math. 5]

$$\text{ConditionNumber} = \|(S^tS)\| \cdot \|(S^tS)^{-1}\| \quad \text{(Formula 5)}$$

With respect to the definition of the norm, there are L1 norm (the sum of the absolute values of the matrix elements), L2 norm (the sum of the squares of the matrix elements) and the like. The condition number represented by (Formula 5) indicates whether the conditions for deriving the inverse through numerical analysis are good or bad, and a larger condition number indicates that the accuracy of the derived inverse is lower. In other words, since the accuracy of the inverse of $(S^tS)$ used for deriving the matrix M by (Formula 3) is low, the reliability of the matrix M derived from the inverse is thus low. That the condition number derived by (Formula 5) is large means that the degree of the overlap of the fluorescence spectra in the fluorescence spectrum matrix S is considerable for some reason such as noise of the detection system or the deterioration of the migration medium and the reliability of the measured fluorescence spectrum matrix S is low.

<Explanation of the Step 608>

Next, an example of the fluorescence intensity calculation process in FIG. 6 is explained.

In the flow shown in FIG. 6, the fluorescence intensities of the fluorescent dyes are calculated using the matrix M (the step 608). In this Example, this process is conducted by the fluorescence intensity calculation unit 110. In the fluorescence intensity calculation process (the step 608), the elements $C_F$, $C_V$, $C_N$, $C_P$ and $C_L$ of the fluorescence intensity vector C are determined by (Formula 1) using the matrix M obtained in the step 607, as in the process described in the step 602. When the fluorescence intensity vectors C are determined for the respective times and plotted as time series data of the signal intensities for each fluorescent dye, fluorescence intensity waveforms such as those shown in FIG. 9 and FIG. 10 can be obtained.

<Explanation of the Step 609>

Next, an example of the STR analysis process in FIG. 6 is explained.

In the flow shown in FIG. 6, STR analysis is conducted using the fluorescence intensity waveform of each fluorescent dye (the step 609). In this Example, this process is conducted by the STR analysis unit 111.

Figure 20:
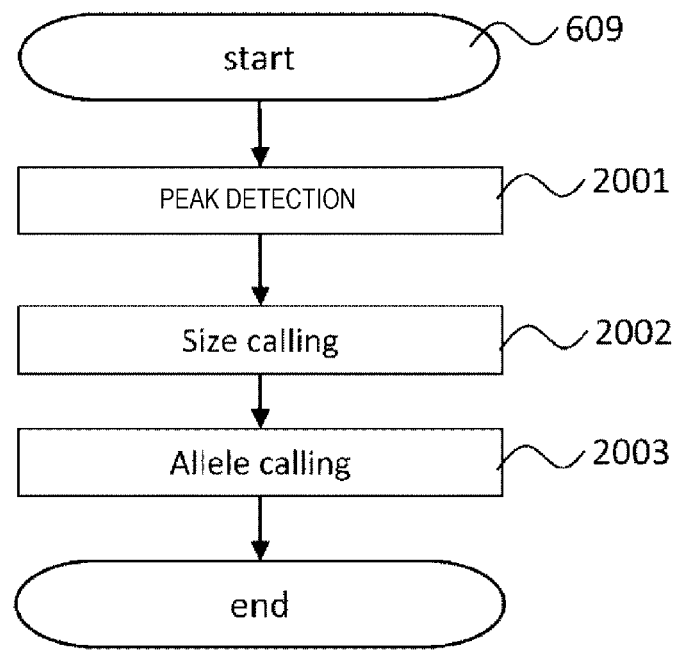
[FIG. 20] A flowchart of the STR analysis process according to Example 1.

FIG. 20 is a flowchart of the STR analysis process. As shown in the figure, the STR analysis process contains three steps: peak detection (a step 2001), size calling (a step 2002) and allele calling (a step 2003). Among the steps, peak detection (the step 2001) and size calling (the step 2002) are similar to the respective processes of peak detection (the step 603) and size calling (the step 604) which are described above. That is, since the matrix M has been changed in the step 607 and the fluorescence intensity waveforms have been changed in the step 608 after the processes of the step 603 and the step 604, the peak detection and size calling processes are conducted again.

Next, the process of allele calling (the step 2003) is explained. Allele calling is a process of fine adjustment of the relation of an allele (corresponding to the number of repeating units of STR, as described above) and the DNA fragment length. In this Example, by selecting the kind of reagent used as the allelic ladder, the information about all the loci contained in the allelic ladder (see FIG. 15) has already been obtained, and the relation between an allele and the DNA fragment length is derived from the allelic ladder information. However, a slight discrepancy generally arises between the DNA fragment length derived from a peak in a fluorescence intensity waveform of an actual allelic ladder (FIG. 9) and the corresponding DNA fragment length contained in the allelic ladder information shown in FIG. 15. The discrepancy is stored in the storage unit 104 for each allele as the offset information. Through fine adjustment of the allelic ladder information of FIG. 15 using the offset information, the relation between the allele and the DNA fragment length is finely adjusted, and the accuracy of the allele determination for a peak of a fluorescence intensity of an actual sample improves.

In summary, in the STR analysis process (the step 609), peaks are detected from the fluorescence intensity waveforms of an actual sample (the step 2001), the relational expression of the peak time and the DNA fragment length is derived from the peak times of the size standard among the peaks and the information about the known DNA fragment lengths (the step 2002), the relations between the allele and the DNA fragment length are finely adjusted by determining the DNA fragment lengths of the known alleles in the allelic ladder, and the alleles are determined from the peaks of the fluorescence intensities of the actual sample based on the relations (the step 2003).

The alleles for all the loci are determined in this manner, and the combination pattern of the alleles is the information concerning the genotypes to identify an individual.

As described above, in Example 1, the reference fluorescence spectra are obtained using the size standard and the allelic ladder, the shift amount from the reference fluorescence spectra is determined referring to the fluorescence spectra of the size standard, the fluorescence spectra of all the capillaries are calculated by shifting the reference fluorescence spectra by the shift amount, and the matrices M are calculated from the fluorescence spectra. The fluorescence intensity waveforms of the respective fluorescent dyes can be obtained from the measured spectra using the matrices. Since by such a method, it is possible to conduct spectral calibration simultaneously with electrophoresis of the actual sample without conducting electrophoresis using a special matrix standard and obtain the fluorescence intensity waveforms, the time and costs required for spectral calibration can be saved.

Example 2

The genotype analyzer according to Example 2 of the invention is explained.

In the genotype analyzer according to Example 1, using the capillary in which electrophoresis of the allelic ladder was carried out as the reference capillary, the single-color peak times of the allelic ladder and the size standard of the reference capillary were extracted, and the spectra at the times were used as the reference fluorescence spectra. Then, the reference fluorescence spectra were shifted, and thus the fluorescence spectra of all the capillaries other than the reference capillary were determined to calculate the matrices M for all the capillaries.

As described above, however, ideally, the fluorescence spectrum of a fluorescent dye can be determined uniquely from the kind of fluorescent dye, the wavelength of the excitation light for the fluorescent dye and the properties of the migration medium of the capillary, irrespective of the apparatus.

Thus, Example 2 of the invention is characterized in that the reference fluorescence spectra are determined by measuring in advance the fluorescence spectra, which are determined by the kinds of fluorescent dye, the wavelengths of the excitation light, the properties of the migration medium and the like as described above, comparing with the fluorescence spectra and correcting, instead of determining the reference fluorescence spectra only from the single-color peak times of the allelic ladder. The unique fluorescence spectra, which are measured in advance, are referred to as ideal fluorescence spectra below. The ideal fluorescence spectrum waveforms are either measured by the manufacturer of the apparatus in advance before shipping the genotype analyzer or measured by a service engineer or the like when the apparatus is installed and stored in the apparatus. Details of Example 2 of the invention are explained below, referring to the drawings.

The constitution of the genotype analyzer according to Example 2 is similar to the constitution of Example 1 shown in FIG. 1. The only difference between Example 1 and Example 2 is the difference in the process of determining the reference fluorescence spectra conducted by the matrix calculation unit 109, and the other processes are similar to those of Example 1.

Figure 21:
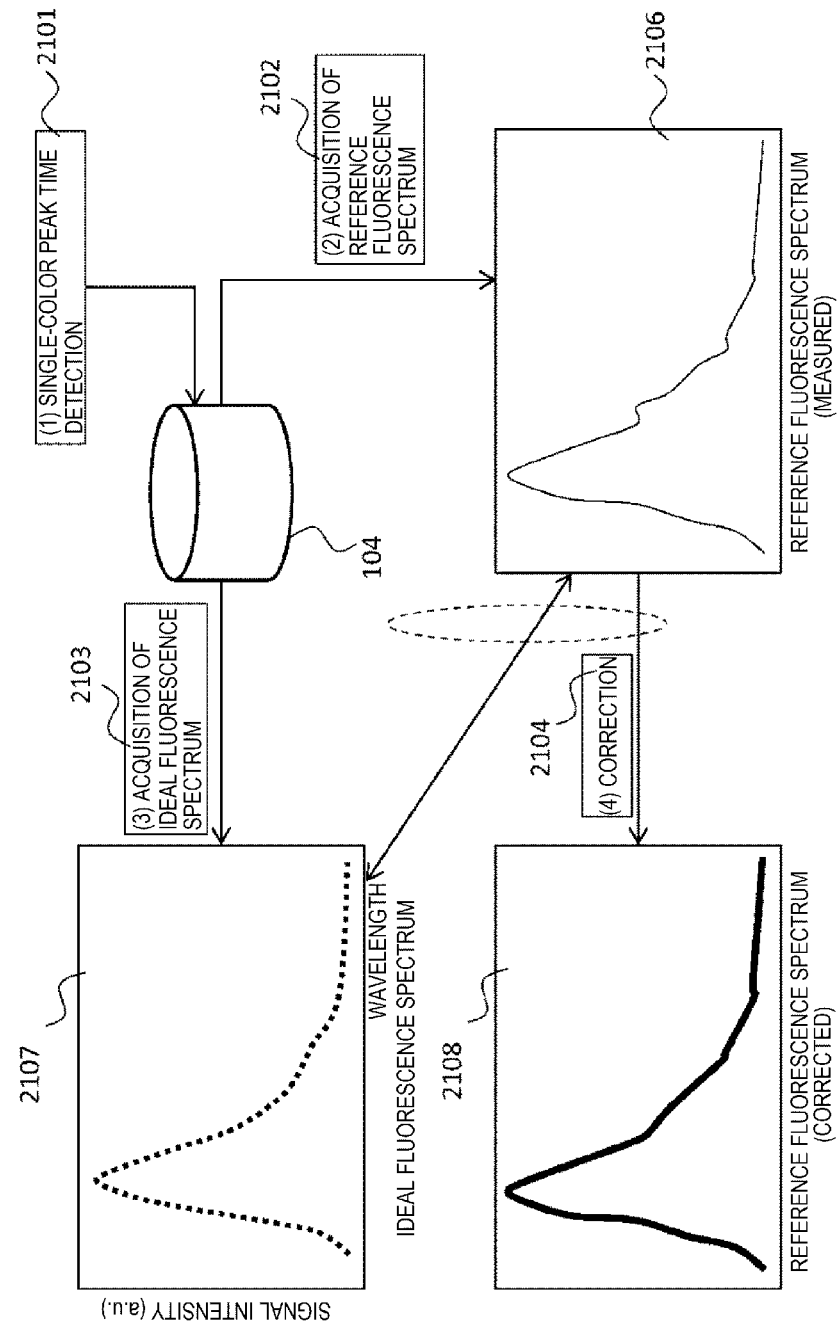
[FIG. 21] A figure for explaining a summary of acquisition of a reference fluorescence spectrum according to Example 2.

FIG. 21 is a figure showing the concept of the process of calculating the reference fluorescence spectra in the matrix calculation unit 109 according to Example 2.

The processes of single-color peak time detection (a step 2101) and acquisition of fluorescence spectra (a step 2102) in the figure are similar to the single-color peak time detection (the step 1401) and the acquisition process of the reference fluorescence spectra (the step 1402) in the acquisition process of the reference fluorescence spectra (the step 605) shown in FIG. 14, and thus the explanations of the processes are not given here.

Next, in the acquisition process of the ideal fluorescence spectra in FIG. 21 (a step 2103), an ideal fluorescence spectrum 2107 stored in the storage unit 104 is obtained. As described above, each ideal fluorescence spectrum 2107 is either measured by the manufacturer of the apparatus in advance before shipping the genotype analyzer or measured by a service engineer or the like when the apparatus is installed and is stored in the storage unit 104 in the apparatus. In this regard, although the spectrum of only one kind of fluorescent dye is illustrated in the figure as the fluorescence spectrum, a similar process is conducted for all the fluorescent dyes.

Next, in the correction process in FIG. 21 (a step 2104), a reference fluorescence spectrum 2106 is corrected based on the comparison of the ideal fluorescence spectrum 2107 and the reference fluorescence spectrum 2106, thereby obtaining a final reference fluorescence spectrum 2108.

Figure 22:
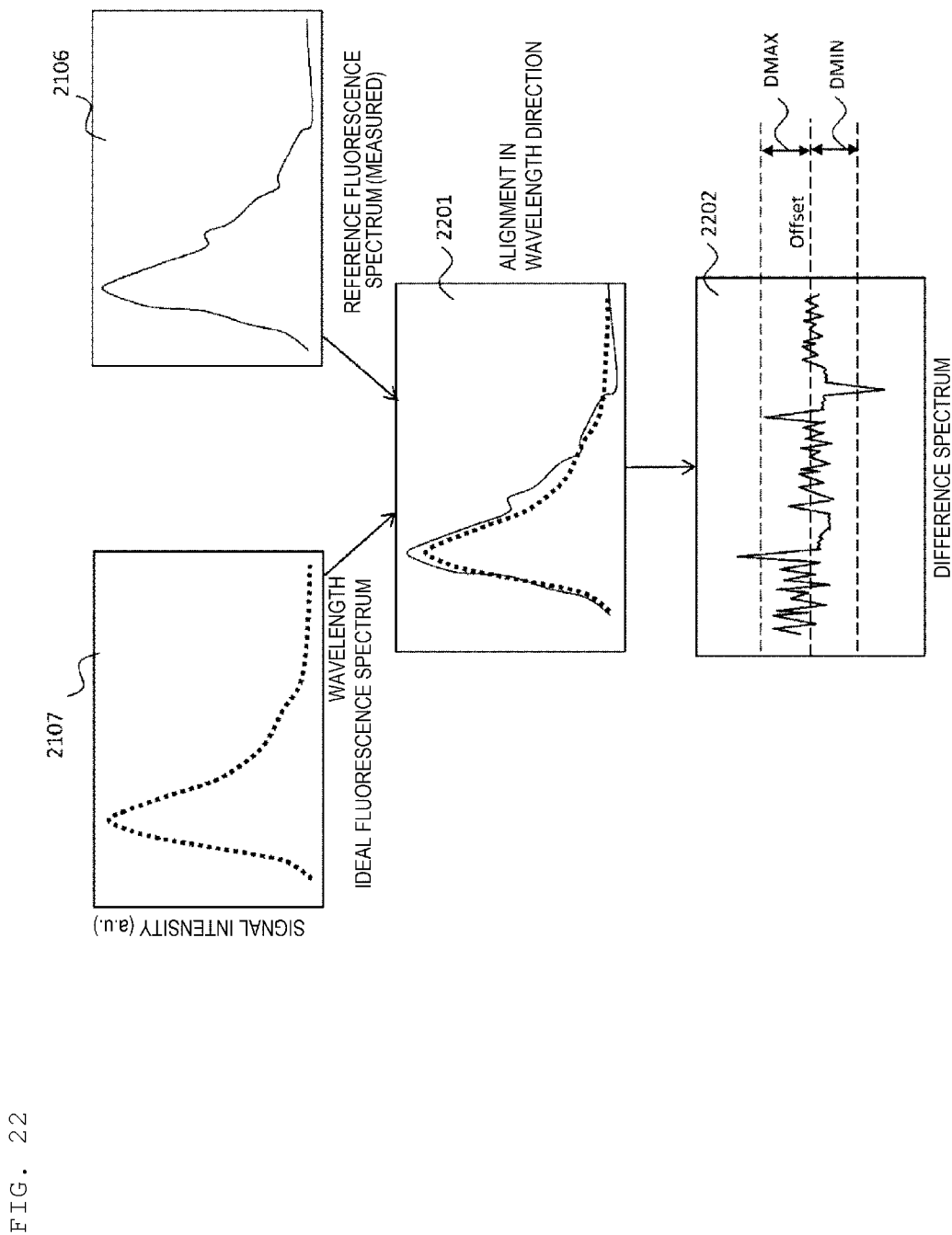
[FIG. 22] A figure for explaining an example of correction of a reference fluorescence spectrum according to Example 2.

Referring to FIG. 22, an example of the correction process (the step 2104) is explained. In the figure, the reference fluorescence spectrum 2106 and the ideal fluorescence spectrum 2107 are data each obtained from the spectra stored in the storage unit 104, as described above. First, alignment is performed in the wavelength direction (2201). For this process, it is possible to employ a method which is similar to the process of calculating the shift amount from the reference capillary (the step 1703 in FIG. 17) in the fluorescence spectrum calculation procedure (the step 606 in FIG. 6) in Example 1. That is, by calculating a cross-correlation function of the spectra and determining a shift amount at which the value is the largest, the discrepancy between the spectra can be resolved, in other words alignment can be performed. Alternatively, Gaussian fitting described above may be applied to the spectra, and the difference between the peak centers may be used as the shift amount.

After the alignment in the wavelength direction, a difference spectrum is derived by subtracting the ideal fluorescence spectrum 2107 from the reference fluorescence spectrum 2106 (2202). The figure shows the process of clipping the value of the difference spectrum (2202) with a maximum difference (DMAX) and a minimum difference (DMIN) which are set in advance. In the figure, DMAX and DMIN are the maximum and minimum of the acceptable difference based on the offset value in the figure, respectively, where DMAX is the maximum of the plus difference and DMIN is the minimum of the minus difference. In the figure, the offset is a value indicating the general difference in the signal intensity of the reference fluorescence spectrum 2106 relative to the ideal fluorescence spectrum 2107, and the average of the difference spectrum may be used as the offset, for example. Based on the offset, the area of the difference spectrum is set as [Offset+DMIN, Offset+DMAX]. Data among the difference spectrum data which are outside the area are clipped by the maximum or the minimum of the area.

Thus, in the correction process of the reference fluorescence spectra (the step 2104) of Example 2, by determining an acceptable width of the difference from the ideal fluorescence spectrum in advance and conducting the clipping process, it is possible to reduce the noise of the spectra caused during the measurement. In this regard, the correction process above is an example, and the correction process is not limited to the example. As long as the reference fluorescence spectra are corrected based on the comparison with the ideal fluorescence spectra, various processes can be employed.

Although the above example of the correction process of the reference fluorescence spectra (the step 2104) is an example in which the difference from the ideal fluorescence spectrum is clipped, when the reliability of a measured reference fluorescence spectrum is determined to be low, the reference fluorescence spectrum may be replaced with the ideal fluorescence spectrum in the correction process (the step 2104).

Figure 23:
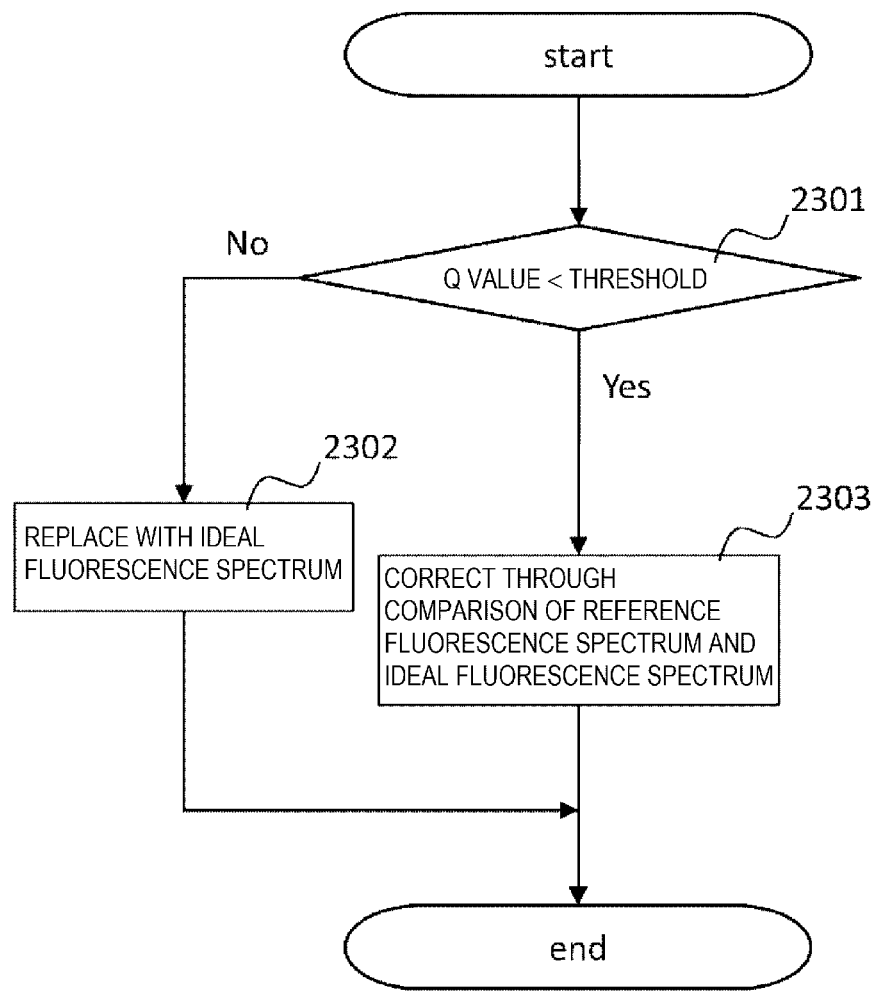
[FIG. 23] A figure for explaining an example of the determination process during correction of a reference fluorescence spectrum according to Example 2.

An example of such a process is explained using FIG. 23. In the figure, a value indicating the reliability of a reference fluorescence spectrum (Q value) and a threshold which is determined in advance are compared in a step 2301. In the figure, it is supposed that the larger the Q value, the lower the reliability of the reference fluorescence spectrum. An example of the index for the Q value is the condition number of the matrix derived from the product of the transpose of the fluorescence spectrum matrix S multiplied by the matrix S, as shown by (Formula 5). As described above, that the condition number obtained by (Formula 5) is large means that the degree of the overlap of the fluorescence spectra in the fluorescence spectrum matrix S is considerable for some reason such as noise of the detection system and the deterioration of the migration medium and the reliability of the measured fluorescence spectrum matrix S is low.

Accordingly, when the Q value is larger than the threshold as a result of the comparison in the step 2301, it is determined that the reliability of the reference fluorescence spectrum is low, and thus the reference fluorescence spectrum is replaced with the ideal fluorescence spectrum (a step 2303) without using the measured reference fluorescence spectrum. However, according to the need, the ideal fluorescence spectrum may be aligned in the wavelength direction with the reference fluorescence spectrum, as shown in FIG. 21.

On the other hand, when the Q value is smaller than the threshold as a result of the comparison in the step 2301, it is determined that the reliability of the reference fluorescence spectrum is high, and the correction process of the reference fluorescence spectrum described in the explanation of FIG. 22 is performed (the step 2303).

In this regard, the replacement of a reference fluorescence spectrum with the ideal fluorescence spectrum (a step 2302) described above can also be applied to genotype analysis using no allelic ladder. In other words, as long as the application of the genotype analysis does not require high nucleotide resolution in STR analysis (for example, a test of foods), the alleles can be identified without using the allelic ladder. In such a case, the reference fluorescence spectra cannot be obtained using the information of the allelic ladder, unlike in Example 1. In this case, using the ideal fluorescence spectra as the reference fluorescence spectra in the step 2302 to determine the shift amount for each capillary, the fluorescence spectra can be obtained.

As described above, the genotype analyzer according to Example 2 of the invention is characterized in that the reference fluorescence spectra are determined by measuring in advance the ideal fluorescence spectra, which are determined by the kinds of fluorescent dye, the wavelengths of the excitation light, the properties of the migration medium and the like, comparing with the ideal fluorescence spectra and correcting, instead of determining the reference fluorescence spectra only from the single-color peak times of the allelic ladder, and thus spectral calibration is conducted. By correcting the reference fluorescence spectra through the comparison with the ideal fluorescence spectra, it is possible to reduce the influence of the noise and the like caused during the measurement during the spectral calibration.

Example 3

The genotype analyzer according to Example 3 of the invention is explained.

In the genotype analyzers according to Example 1 and Example 2, the capillary in which electrophoresis of the allelic ladder was performed was used as the reference capillary, and the reference fluorescence spectra of the reference capillary were determined. Then, the shift amounts between the reference fluorescence spectra and the spectra of the capillaries other than the reference capillary were determined, and the reference fluorescence spectra were shifted by the respective amounts to determine the fluorescence spectra of all of the capillaries other than the reference capillary, thereby calculating the matrices M of all the capillaries.

However, in Example 1 and Example 2, since the fluorescence spectra of a capillary are determined using the shift from the reference fluorescence spectrum of the reference capillary as described above, it is not supposed that the shapes of the fluorescence spectra vary among the capillaries. In practice, due to some factors of the optical system or the measurement system, the shapes of the fluorescence spectra may vary slightly.

Therefore, Example 3 of the invention is characterized in that the fluorescence spectra are determined using the spectra obtained by electrophoresis of an actual sample for a capillary, instead of the shift from the reference fluorescence spectrum.

Details of the genotype analyzer according to Example 3 are explained below, referring to the drawings. The constitution of the genotype analyzer according to Example 3 is similar to the constitution shown in FIG. 1.

Figure 24:
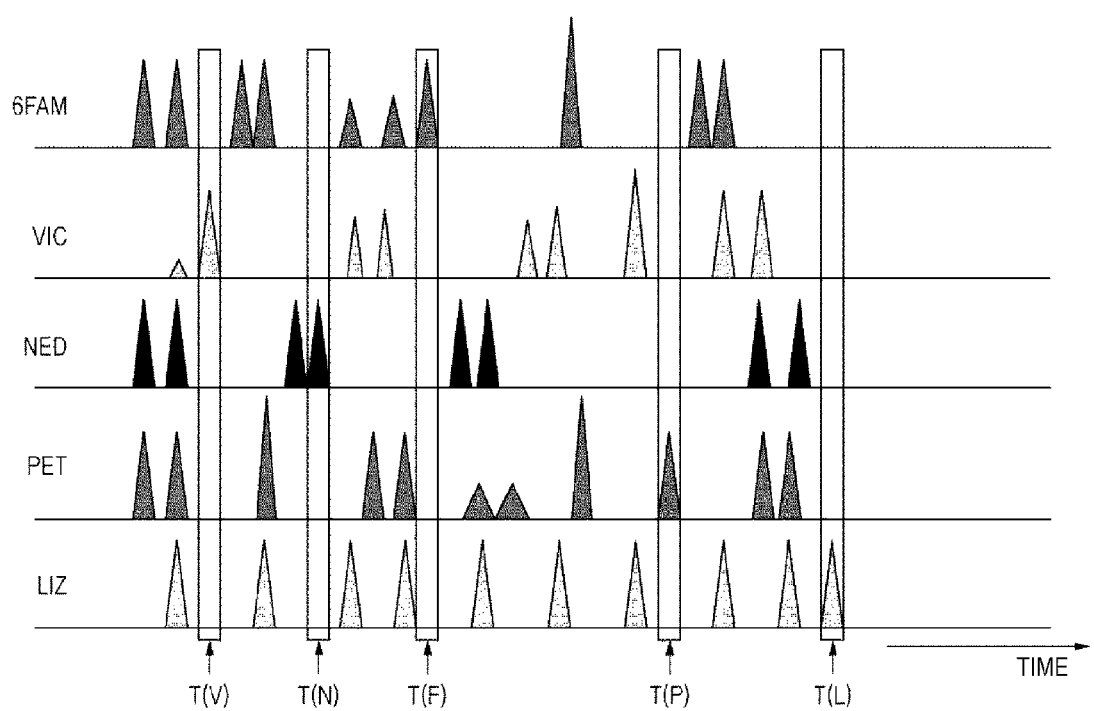
[FIG. 24] A figure for explaining the concept of acquisition of fluorescence spectra according to Example 3.

FIG. 24 is a figure showing the concept of the process of determining the fluorescence spectra using the spectra obtained by electrophoresis of an actual sample.

In Example 1, as shown in FIG. 13 and FIG. 16, the single-color peak times of the respective fluorescent dyes were detected from the waveforms of the fluorescence intensities of the allelic ladder, and the spectra at the single-color peak times were used as the fluorescence spectra of the respective fluorescent dyes.

Similarly, in Example 3, the single-color peak times are detected from the waveforms of the fluorescence intensities obtained by electrophoresis of an actual sample to be measured in a capillary, and the spectra at the single-color peak times are used as the fluorescence spectra of the respective fluorescent dyes. FIG. 24 shows an example in which single-color peak times T(F), T(V), T(N), T(P) and T(L) are extracted for five fluorescent dyes, 6FAM, VIC, NED, PET and LIZ, respectively, based on the waveforms of the fluorescence intensities obtained by electrophoresis of an actual sample. There is a peak for only one fluorescent dye at each of the times, and such a time should be detected.

Figure 30:
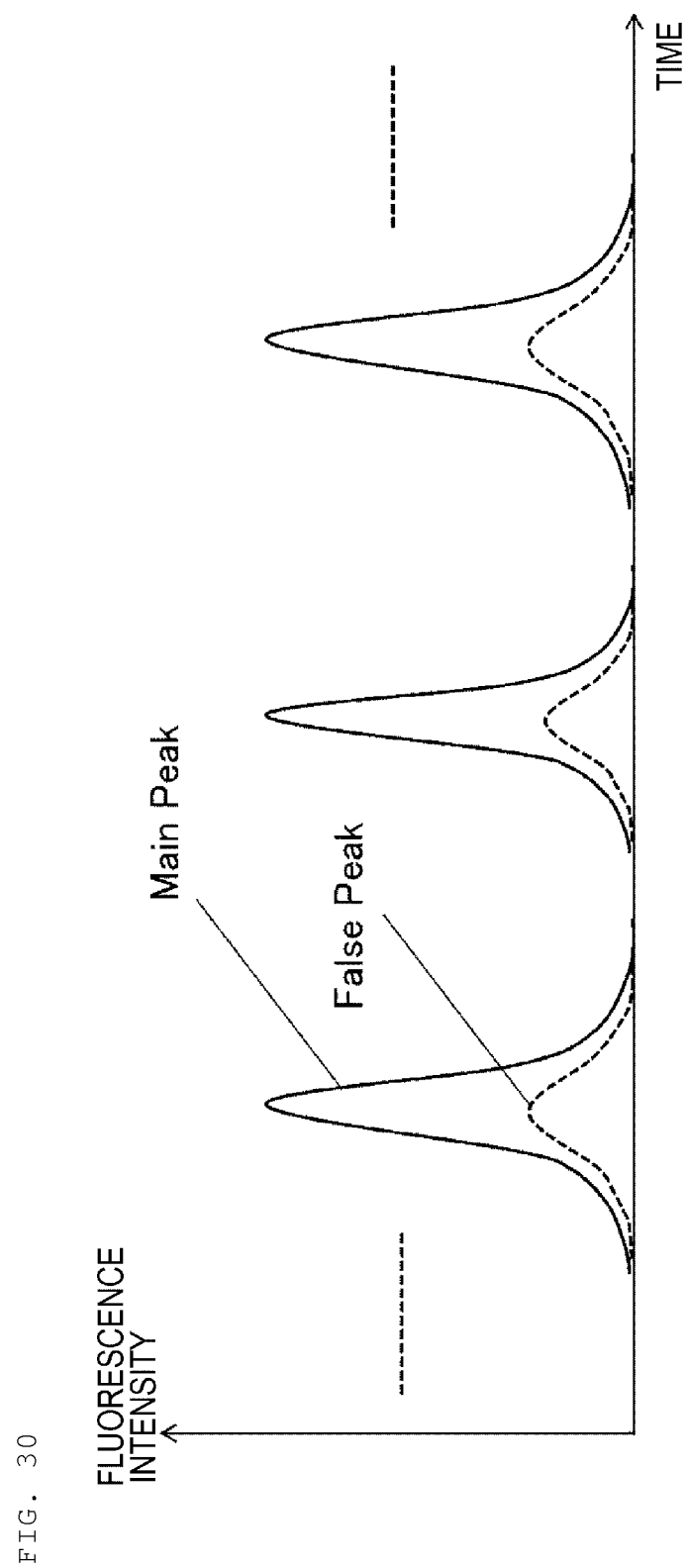
[FIG. 30] A figure for explaining the concept of a false peak.

However, at such a single-color peak time, in addition to a main peak of a fluorescent color, a false peak may be observed at the same peak position as that of the main peak, when the initial matrix is not appropriate (see FIG. 30). The false peak is caused by the overlap of a fluorescence spectrum of another color, and significant influence of the overlap is observed when the initial matrix is not appropriate. Moreover, when there are two or more main peaks, false peaks are observed for all the main peaks.

Peaks of different fluorescent colors may appear at the same time in STR analysis. In such a case, it is not possible to determine that a smaller peak is the false peak of a larger peak. This is because, since the small peak is the true peak, a matrix which excludes the true peak may be calculated.

Accordingly, it is desirable to carefully determine whether a peak is a false peak or a true peak. Example conditions (C1) to (C4) for determining that a peak is a false peak are shown below, referring to FIG. 32.

(C1): The difference between the peak time of the main peak (T1) and the peak time of the false peak (T2) is within a time difference which is determined in advance (namely, T1≈T2) (FIG. 32(a)).

(C2): The peak height of the main peak (H1), the peak height of the false peak (H2) and the ratio thereof (H1/H2) are within ranges which are determined in advance (FIG. 32(b)).

(C3): The number of patterns of the main peak and the false peak which satisfy the above conditions is a number which is determined in advance or larger (FIG. 32(c)).

(C4): There is no individual main peak (FIG. 32(c)).

And the like.

The conditions (C3) and (C4) are believed to be useful for preventing the detection of a true peak as a false peak by mistake, because the probability that all the true peaks of different fluorescent colors are observed at the same times.

In Example 3, patterns of false peaks satisfying the above conditions are searched from the time series fluorescence intensity waveforms, and the times of the false peaks are used as the single-color peak times to determine the fluorescence spectra.

Figure 32:
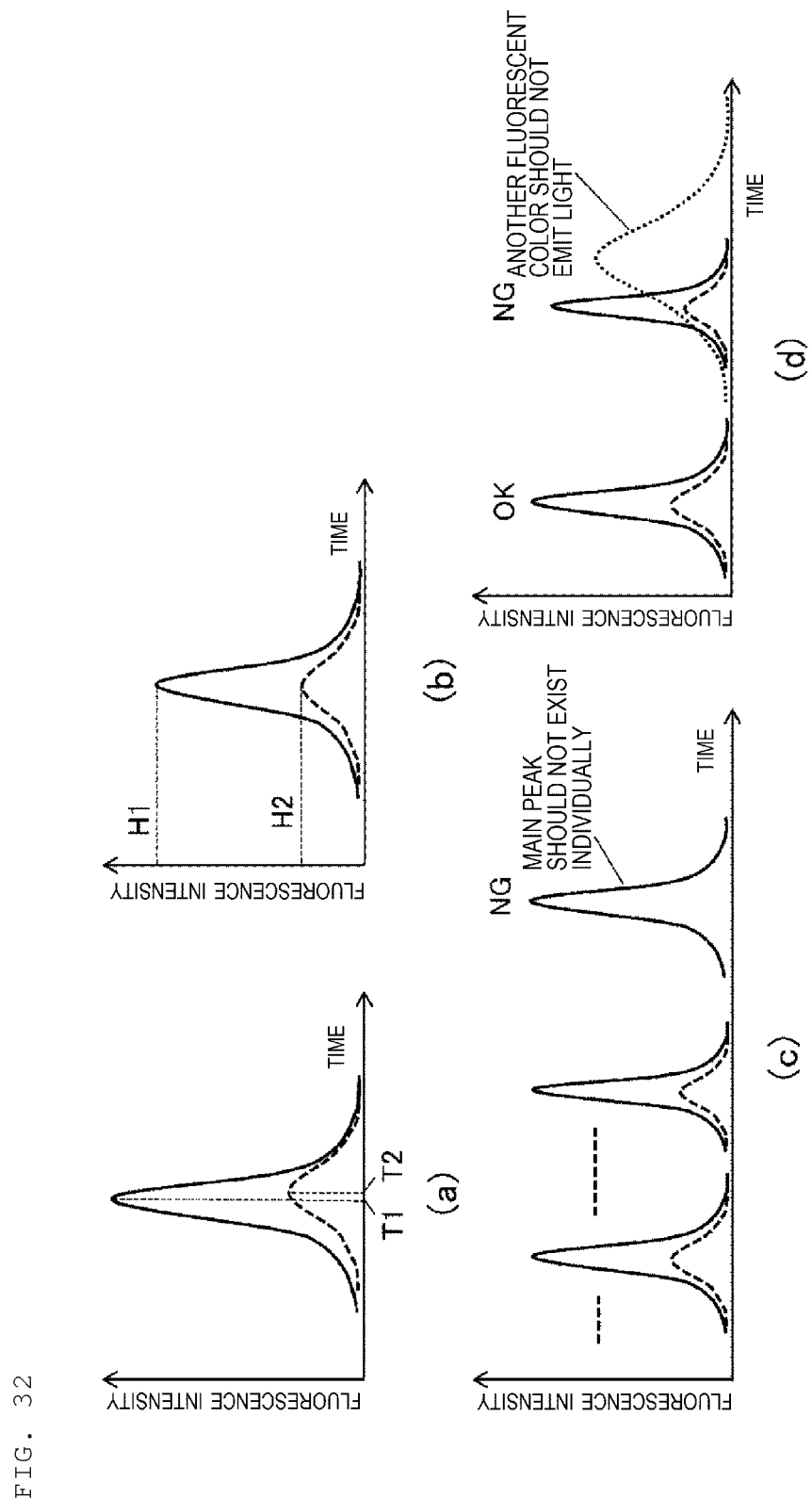
[FIG. 32] A figure for explaining determination conditions for a false peak of the genetic analyzer according to Example 5.

In this regard, among the two or more false peak times found above, it is desirable to select a time at which the fluorescent dyes other than the fluorescent colors of the main peak and the false peak do not emit light, to use as the single-color peak time (FIG. 32(*d*)).

Although an example in which there is one false peak for one main peak is shown in FIG. 30 and FIG. 32, similar conditions can be applied even when there are two or more false peaks for one main peak. In addition, the conditions are examples, and the invention is not limited to the conditions.

With respect to electrophoresis of an actual sample, however, there is no guarantee that single-color peak times suitable for determining the fluorescence spectra can always be obtained, due to the characteristics of the genotypes contained in the sample, the excess or shortage of the DNA concentration of the sample and the like. In other words, for the reason that peak positions of different fluorescent dyes overlap or the width of a peak is large, a phenomenon that there is no false peak derived from only one fluorescent dye or a phenomenon that the peak intensities are too small or too large may arise. Moreover, when the initial matrix is appropriate, such false peaks are not observed.

Therefore, Example 3 is characterized by determining whether or not desirable single-color peak times could be detected from an actual sample and then determining the fluorescence spectra using the spectra of the actual sample only when there are single-color peaks.

Figure 25:
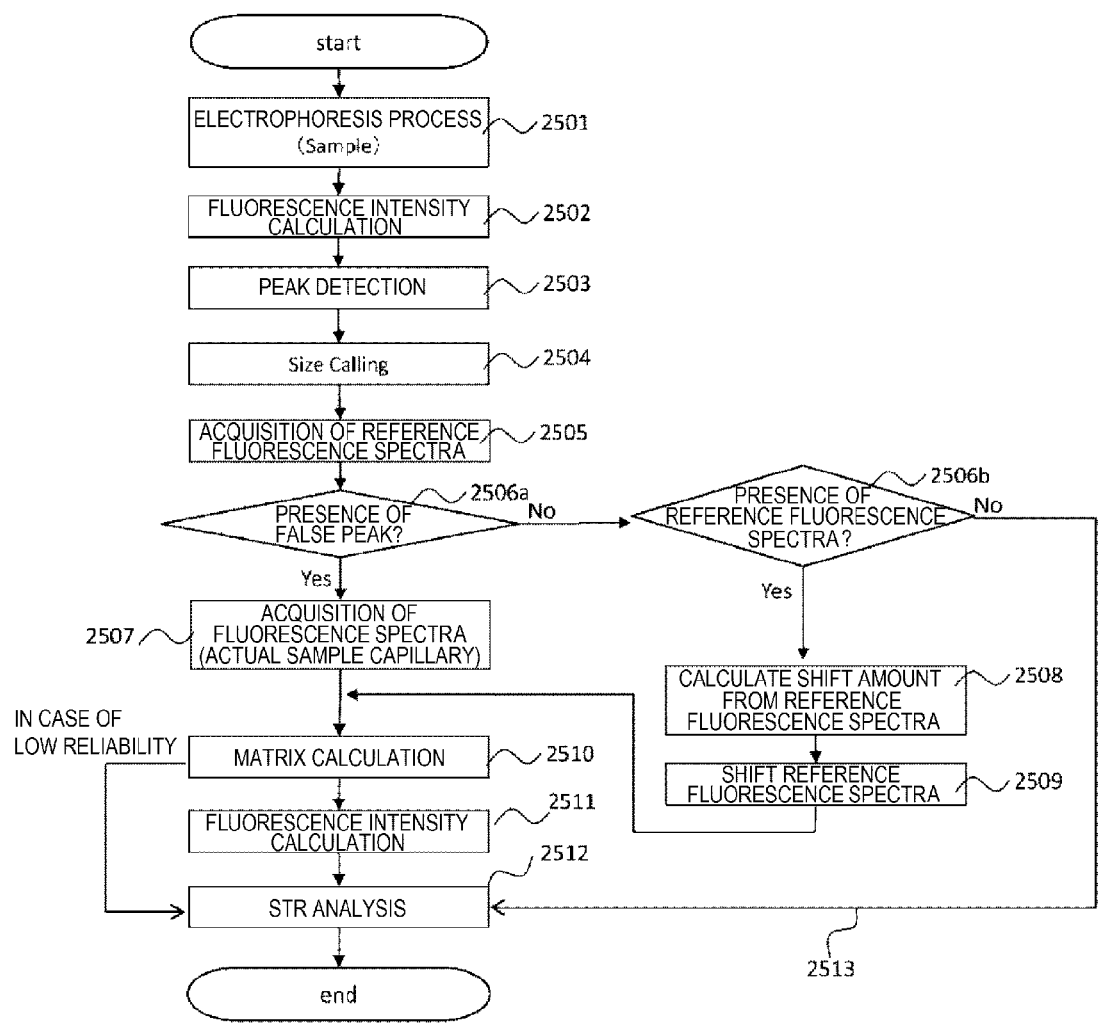
[FIG. 25] A flowchart of the process of the genotype analyzer according to Example 3.

The process flow of the genotype analyzer according to Example 3 is shown in FIG. 25. Electrophoresis is performed in the capillaries of all the samples including the allelic ladder and the control samples in a step 2501. The electrophoresis process is similar to the electrophoresis process in Example 1 (the step 601 in FIG. 6).

Next, in a step 2502, the fluorescence intensities are calculated based on the spectrum data of the obtained electrophoresis results. This process is similar to the fluorescence intensity calculation process in Example 1 (the step 602 in FIG. 6), and the fluorescence intensity waveforms of the fluorescent dyes can be obtained in accordance with the calculation of (Formula 1) using the initial matrix M.

Next, in a step 2503, a peak detection process is conducted with respect to the fluorescence intensity waveforms obtained in the step 2502. This process is similar to the peak detection process in Example 1 (the step 603 in FIG. 6), and known means such as Gaussian fitting can be used.

Next, in a step 2504, a size calling process is conducted. This process is similar to the size calling process in Example 1 (the step 604 in FIG. 6), and the relational expression of the electrophoresis time and the DNA fragment length "y=f(t)" is obtained from the peak times of the fluorescent dye assigned to the size standard (LIZ in this Example) and the information about the known DNA fragment lengths.

Next, in a step 2505, the reference fluorescence spectra are obtained. This process is similar to the acquisition process of the reference fluorescence spectra in Example 1 (the step 605 in FIG. 6). Using the capillary containing the allelic ladder as the reference capillary, the single-color peak times of the reference capillary are detected, and the reference fluorescence spectra are obtained. As described in Example 2, the reference fluorescence spectra may be corrected by comparing with the ideal fluorescence spectra (see FIG. 21). Even when the single-color peak times are not detected for the reference capillary and thus the reference fluorescence spectra cannot be obtained, a step 2506*a* is conducted.

Next, in the step 2506*a*, the single-color peak times of a capillary containing an actual sample (a capillary other than the reference capillary) are detected, and it is determined whether or not the peaks are single-color peaks desirable for obtaining the fluorescence spectra, in other words, the presence or absence of a false peak is determined. Examples of the criteria for determining whether or not a single-color peak is desirable for obtaining a fluorescence spectrum are (1) the degree of overlap with another fluorescent dye, (2) the peak height and the like.

The criterion for determination based on the degree of overlap with another fluorescent dye of (1) should be based on whether the fluorescence intensity of the other fluorescent dye at the peak time is sufficiently small. Moreover, it is desirable that the peak time is as far as possible from the peak time of the other fluorescent dye.

Concerning the criterion for determination based on the peak height of (2), it is desirable that the intensity of the single-color peak is large enough. In addition, a peak which is too high and exceeds the dynamic range of the optical detection system should be excluded. Accordingly, the upper limit and the lower limit of an acceptable range of the intensity of the single-color peak should be determined in advance, and a time of a peak within the acceptable range should be used.

When there is a single-color peak time which satisfies both of the criteria for determination of (1) and (2) in the determination process of the step 2506*a* (when there is a false peak), the spectrum at the peak time should be obtained and used as a fluorescence spectrum (a step 2507).

When there is no single-color peak time which satisfies both of the criteria for determination of (1) and (2) in the determination process of the step 2506*a* (when there is no false peak), a step 2506*b* is conducted, and when the reference fluorescence spectra have been obtained in the step 2505 (when there are reference fluorescence spectra), a step 2508 is conducted, to conduct a process similar to the fluorescence spectrum calculation process described in the step 606 in FIG. 17 in Example 1. That is, from the waveforms of the spectrum of the size standard among the reference fluorescence spectra of the reference capillary and the spectrum of the size standard of another capillary, the shift amount of the spectra of the other capillary from the reference fluorescence spectra is calculated as shown in FIGS. 19A and B (the step 2508), and the reference fluorescence spectra are shifted by the shift amount to calculate the fluorescence spectra of the other capillary (a step 2509). In this regard, the reference fluorescence spectra in the step 2508 may be the fluorescence spectra of the allelic ladder and the size standard as in Example 1, or when the fluorescence spectra have already been obtained from the actual sample and the size standard in the other capillary, the fluorescence spectra may be used as the reference fluorescence spectra. In addition, the initial fluorescence spectra described above (on the supposition that the initial fluorescence spectra are stored in the storage unit 104) may be used as the reference fluorescence spectra.

When there is no single-color peak time which satisfies both of the criteria for determination of (1) and (2) in the determination process of the step 2506 (when there is no false peak), and when the reference fluorescence spectra have not been obtained in the step 2505 (when there is no reference fluorescence spectrum) or when the presence or absence of the reference fluorescence spectra does not matter, a path 2513 is taken, and STR analysis may be conducted with respect to the fluorescence intensity waveforms to which the initial matrix is applied without newly calculating the matrix M.

Then, a matrix calculation process is conducted in a step 2510. This process is similar to the matrix calculation process in Example 1 (the step 607 in FIG. 6), and the matrix M is calculated by (Formula 2) and (Formula 3) based on the obtained fluorescence spectra. As in the step 607, the reliability of the matrix M is evaluated by (Formula 5), and when the reliability of the matrix M is low, STR analysis may be conducted with respect to the fluorescence intensity waveforms to which the initial matrix is applied through the path 2513 without using the matrix M.

Then, a fluorescence intensity calculation process is carried out in a step 2511. This process is similar to the fluorescence intensity calculation process in Example 1 (the step 608 in FIG. 6), and the fluorescence intensity waveforms of the fluorescent dyes are derived by multiplying the spectra at the respective times by the matrix M according to (Formula 1).

Then, STR analysis is conducted in a step 2512. This process is similar to the STR analysis process in Example 1 (the step 609 in FIG. 6), and the alleles for all the loci are determined by conducting the peak detection process (the step 2001), the size calling process (the step 2002) and the allele calling process (the step 2003) as shown in FIG. 20. The combination pattern of the alleles is the information of the genotypes for identifying an individual.

As described above, the genotype analyzer according to Example 3 of the invention is characterized in that spectral calibration is performed by detecting the single-color peaks using the spectra obtained by electrophoresis of an actual sample for each capillary and determining the fluorescence spectra based on the single-color peaks, instead of the shift from the reference fluorescence spectra. According to Example 3, by using excellent single-color peaks of an actual sample, it becomes possible to reflect the slight difference in the fluorescence spectrum waveforms among the capillaries and to perform spectral calibration with higher accuracy, as compared to Example 1 and Example 2.

Moreover, with the genotype analyzer according to Example 3 of the invention, since the reference fluorescence spectra are not used, spectral calibration can be performed also for genotype analysis which does not use the allelic ladder, using the electrophoresis results of an actual sample.

Example 4

The genotype analyzer according to Example 4 of the invention is explained.

In Example 1 and Example 2, the reference fluorescence spectra were obtained using the reference capillary, and with respect to the other capillaries, the fluorescence spectra of the capillaries were calculated by shifting the reference fluorescence spectra. In Example 3, the single-color peak times were detected using the spectra of electrophoresis of an actual sample in each capillary to obtain the fluorescence spectra. However, also in Example 3, when desirable single-color peak times could not be detected, the fluorescence spectra were calculated by shifting the reference fluorescence spectra as in Example 1 or Example 2.

In the Examples, the shift amount of the reference fluorescence spectra was calculated using the spectra of the size standard. That is, as shown in FIGS. 19A and B, from the spectrum of the size standard of the reference capillary and the spectrum of the size standard of another capillary, the shift amount between the wavelengths of both spectra was calculated.

As a condition for calculating the shift amount using the size standard as described above, it was supposed that the single-color peak times could be detected from the fluorescence intensity waveforms of the size standard without any problem. In practice, however, the peak intensities may be outside the acceptable range due to the insufficiency of the concentration of the size standard in the reference capillary or the other capillaries or the like, or noise of another fluorescent dye may overlap the single-color peak times. In such cases, it is believed to be inappropriate to calculate the shift amount using the size standard.

Thus, Example 4 is characterized by calculating the shift amount between capillaries using the peak patterns of Raman spectra of capillaries filled only with the migration medium before electrophoresis, in order to calculate the shift amount between the reference capillaries.

The process of the genotype analyzer according to Example 4 is explained below, referring to the drawings. The constitution of the genotype analyzer according to Example 4 is similar to the constitution shown in FIG. 1.

Figure 26:
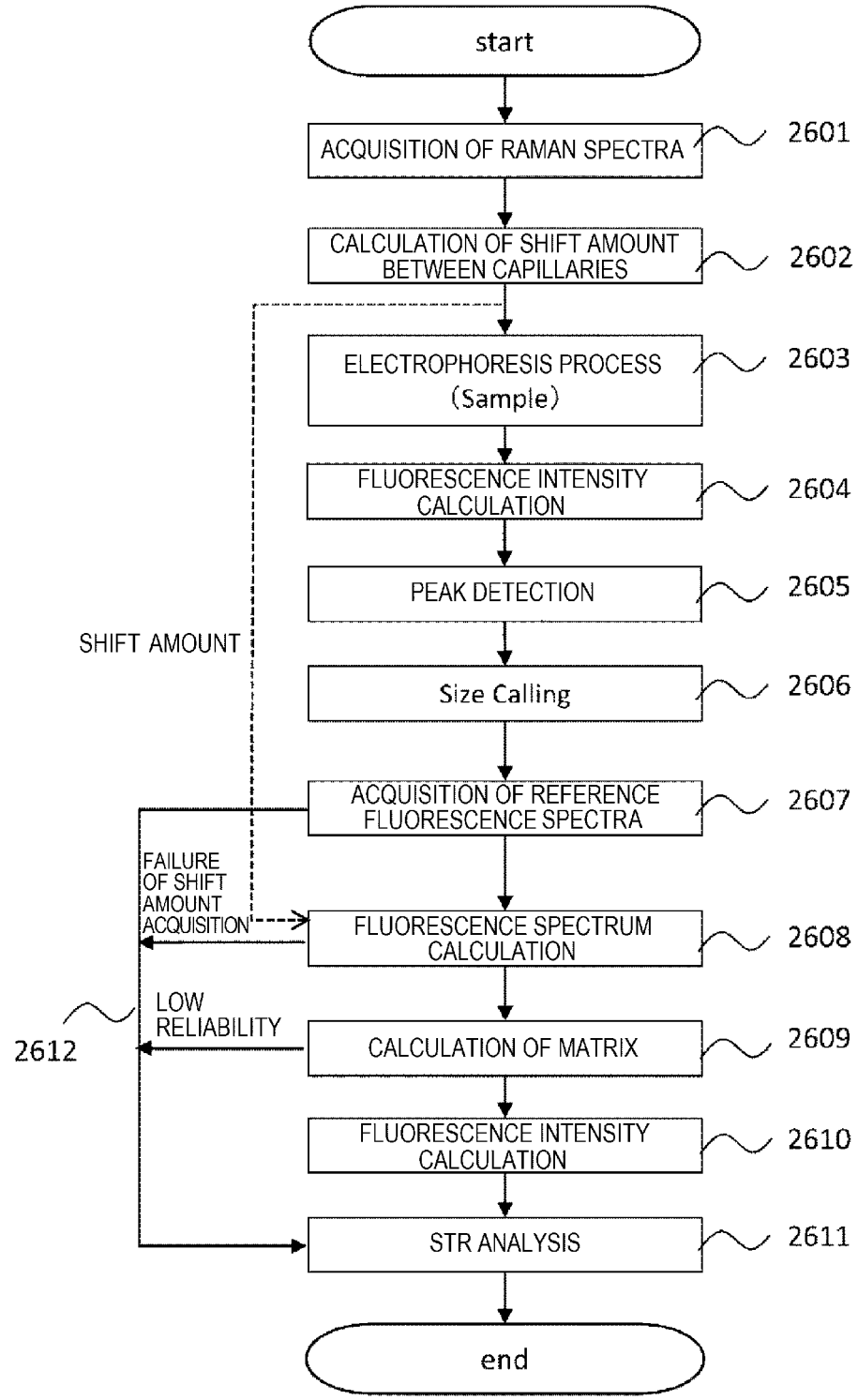
[FIG. 26] A flowchart of the process of the genotype analyzer according to Example 4.

FIG. 26 is a flowchart of the process of the genotype analyzer according to Example 4.

The processes of steps 2601 to 2611 shown in FIG. 26 are explained below.

Step 2601: In the genotype analyzer according to Example 4, Raman spectra are obtained before electrophoresis (the step 2601). When a Raman spectrum is obtained, the Raman-scattered light caused by irradiating a capillary filled with the electrophoresis medium with the light source 514 used for the actual electrophoresis process is detected with the optical detector 515 to obtain a picture image. The picture image is similar to the images shown in FIG. 2, and the Raman spectrum of each capillary can be obtained.

Figure 27:
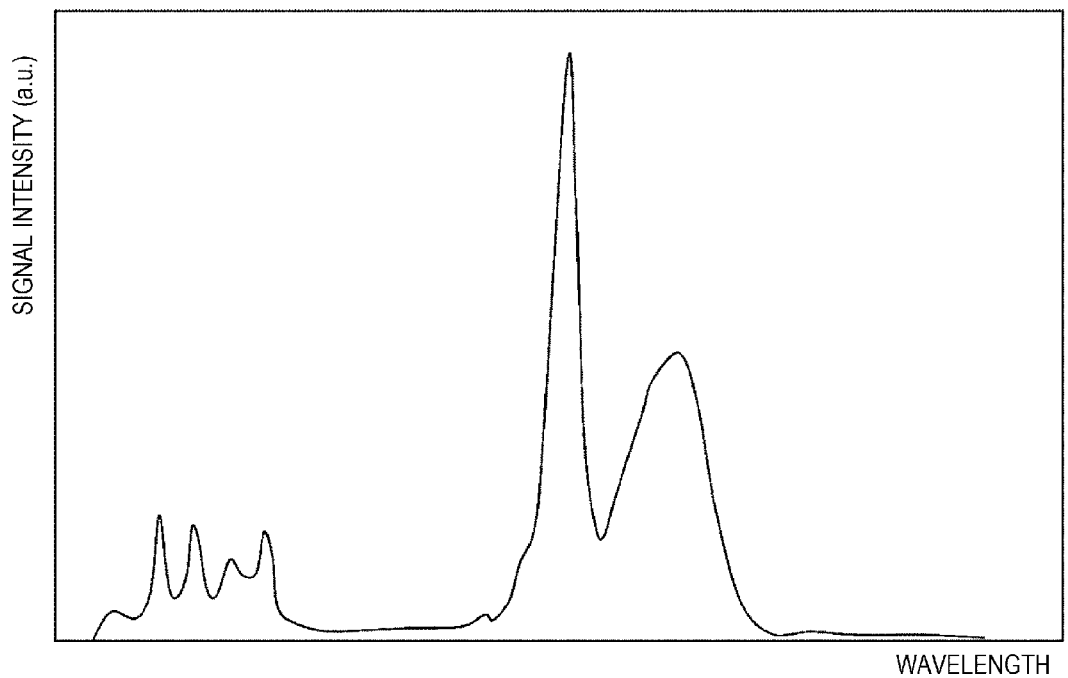
[FIG. 27] A figure showing an example of a Raman spectrum according to Example 4.

An example of the Raman spectrum of a capillary is shown in FIG. 27. The shape of a Raman spectrum depends on the wavelength of the light source and the migration medium and is the same for all the capillaries, but a discrepancy in the wavelength direction may arise due to the positional relation between the capillary and the detector.

Step 2602: Therefore, the shift amount in the wavelength direction between the shapes of the Raman spectra of capillaries is calculated and is used as the shift amount of the reference fluorescence spectra.

As the method for calculating the shift amount, means similar to the calculation process of the shift amount from the reference capillary in Example 1 (the step 1703 in FIG. 17) can be used. That is, as described above, with respect to the Raman spectra, after the data are interpolated through known techniques such as spline interpolation, a cross-correlation function of two spectra may be calculated and the shift amount at which the value becomes the largest may be determined.

Gaussian fitting described above may be applied to the Raman spectra. That is, because the wavelength of the light source and the migration medium are both known for each Raman spectrum, the number of peaks of the Raman spectrum, the peak wavelengths, the ratios of the signal intensities and the like can be determined in advance through measurement. Thus, by detecting the rough positions of the peaks though threshold processing and the like and by applying Gaussian fitting described above (see FIG. 11) to the data around the peaks, the respective peak wavelengths can be determined. Such peak wavelengths may be determined for the Raman spectra of all the capillaries, and the shift amount of the peak wavelengths between capillaries may be calculated.

Step 2603: Next, electrophoresis of an actual sample is performed. This process is similar to the electrophoresis process in Example 1 (FIG. 7). However, the process of filling the migration medium (the step 703) in the figure may be skipped because the capillaries have already been filled with the migration medium in the acquisition process of the Raman spectra (the step 2601).

Step 2604: Next, the fluorescence intensities are calculated based on the spectrum data of the obtained electrophoresis results. This process is similar to the fluorescence intensity calculation process in Example 1 (the step 602 in FIG. 6), and the fluorescence intensity waveforms of the fluorescent dyes can be obtained in accordance with the calculation of (Formula 1) using the initial matrix M.

Step 2605: Next, a peak detection process is conducted with respect to the fluorescence intensity waveforms obtained in the step 2604. This process is similar to the peak detection process in Example 1 (the step 603 in FIG. 6), and known means such as Gaussian fitting can be used.

Step 2606: Next, a size calling process is conducted. This process is similar to the size calling process in Example 1 (the step 604 in FIG. 6), and the relational expression of the electrophoresis time and the DNA fragment length "y=f(t)" is obtained from the peak times of the fluorescent dye assigned to the size standard (LIZ in this Example) and the information about the known DNA fragment lengths.

Step 2607: Next, the reference fluorescence spectra are obtained. This process is similar to the acquisition process of the reference fluorescence spectra in Example 1 (the step 605 in FIG. 6). The capillary containing the allelic ladder is used as the reference capillary, and the single-color peak times of the reference capillary are detected, thereby obtaining the reference fluorescence spectra. As described in Example 2, the reference fluorescence spectra may be corrected by comparing with the ideal fluorescence spectra (see FIG. 21). As in the step 605 of Example 1, when the single-color peak times are not obtained and the reference fluorescence spectra cannot be obtained, the initial fluorescence spectra of the reference capillary (on the supposition that the initial fluorescence spectra are stored in the storage unit 104) may be used as the reference fluorescence spectra. Alternatively, STR analysis may be conducted using the fluorescence intensity waveforms to which the initial matrix is applied through a path 612.

Step 2608: Next, the fluorescence spectra are calculated. For this process, a process similar to the fluorescence spectrum calculation process in Example 1 (the step 606 in FIG. 17) is conducted. However, for the calculation of the shift amount, the shift amount obtained in the step 2602 is used without using the spectra of the size standard as shown in FIG. 19A. The reference fluorescence spectra are shifted by the shift amount to calculate the fluorescence spectra of a capillary other than the reference capillary. When the shift amount could not be obtained properly for reasons such as the low signal intensities of the Raman spectra in the step 2602, the shift amount may be determined from the spectra of the size standard as in the step 606 of Example 1. Moreover, when the shift amount is not obtained in the step 2602 and the shift amount cannot be obtained from the size standard, either (for example, for the reason that there is no single-color peak time for LIZ due to noise and the like), STR analysis may be conducted using the fluorescence intensity waveforms to which the initial matrix is applied through a path 2612 without newly calculating the matrix.

Step 2609: Then, a matrix calculation process is conducted. This process is similar to the matrix calculation process in Example 1 (the step 607 in FIG. 6), and the matrix M is calculated by (Formula 2) and (Formula 3) based on the obtained fluorescence spectra. As in the step 607, the reliability of the matrix M is evaluated by (Formula 5), and when the reliability of the matrix M is low, STR analysis may be conducted with respect to the fluorescence intensity waveforms to which the initial matrix is applied through the path 2612 without using the matrix M.

Step 2610: Then, a fluorescence intensity calculation process is carried out. This process is similar to the fluorescence intensity calculation process in Example 1 (the step 608 in FIG. 6), and the fluorescence intensity waveforms of the fluorescent dyes are derived by multiplying the spectra at the respective times by the matrix M according to (Formula 1).

Step 2611: Then, STR analysis is conducted. This process is similar to the STR analysis process in Example 1 (the step 609 in FIG. 6), and the alleles for all the loci are determined by conducting the peak detection process (the step 2001), the size calling process (the step 2002) and the allele calling process (the step 2003) as shown in FIG. 20. The combination pattern of the alleles is the information of the genotypes for identifying an individual.

As described above, the genotype analyzer according to Example 4 of the invention is characterized by using the Raman spectra measured before electrophoresis, instead of the spectra of the size standard, for determining the shift amount from the reference fluorescence spectra. With this characteristic, even when the single-color peaks cannot be obtained for example because the peak values of the fluorescence intensities of the size standard are small or overlapped with a signal of another fluorescent dye, the fluorescence spectra of each capillary can be calculated by shifting from the reference fluorescence spectra using the shift amount determined from the Raman spectra.

In this regard, when the Raman spectra are used instead of the spectra of the size standard in Example 4, the conditions for the spectra of the size standard serving as the conditions should be determined carefully. In other words, when the quality of the fluorescence intensity data of the size standard of a capillary is extremely low, size calling may not be proper, resulting in the deterioration of the accuracy of the STR analysis results themselves. It is believed that the STR analysis itself should be cancelled for a capillary in such a state. For this reason, when Example 4 is applied, conditions under which the Raman spectra should be used should be determined without deteriorating the quality of size calling. Alternatively, the shift amount may be calculated always by Example 4, independently of the quality of the size standard.

Example 5

The genotype analyzer according to Example 5 of the invention is explained.

In the genetic analyzer according to Example 3, the fluorescence spectra were determined using the spectra obtained by electrophoresis of an actual sample for each capillary. Here, times at which a false peak of a fluorescent color could be observed were searched from the fluorescence intensity waveforms obtained from the actual sample, and the fluorescence spectra were determined using the times as the single-color peak times.

In Example 3, when the single-color peak times were not observed, the capillary in which electrophoresis of the allelic ladder was performed was used as the reference capillary, and the reference fluorescence spectra of the reference capillary were determined, as in the genotype analyzers according to Example 1 and Example 2. Then, the shift amounts between the reference fluorescence spectra and the spectra of the capillaries other than the reference capillary were determined, and the fluorescence spectra of all the capillaries other than the reference capillary were determined by shifting the reference fluorescence spectra by the respective amounts to calculate the matrices M of all the capillaries.

However, as described in Example 3, because the fluorescence spectra of a capillary are determined using the shift from the reference fluorescence spectra of the reference capillary, it is not taken into account that the shapes of the fluorescence spectra vary among the capillaries. In practice, the shapes of the fluorescence spectra may differ slightly due to some factors of the optical system or the measurement system.

Accordingly, when no false peak can be observed, an appropriate matrix may not be obtained from the fluorescence spectra derived by shifting the reference fluorescence spectra. First of all, the initial matrix may be appropriate when no false peak can be observed, and the method in Example 3 may result in a matrix which is less appropriate than the initial matrix.

Thus, the genetic analyzer according to Example 5 is characterized by determining the fluorescence spectra only from the fluorescence intensity waveforms of each capillary without determining the reference fluorescence spectra of the allelic ladder, as a modification of Example 3.

The process of the genotype analyzer according to Example 5 is explained below, referring to the drawings. The constitution of the genotype analyzer according to Example 5 is similar to the constitution shown in FIG. 1.

Figure 31:
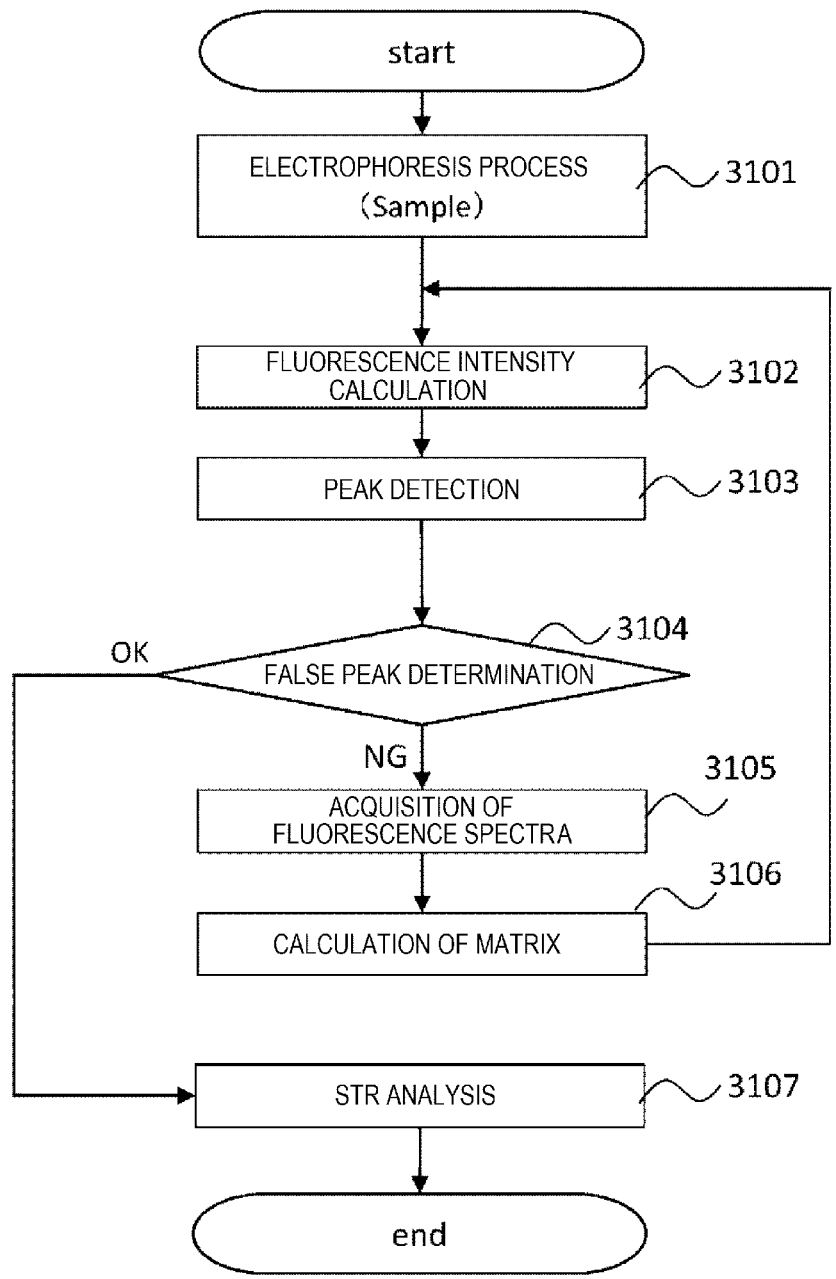
[FIG. 31] A flowchart of the process of the genetic analyzer according to Example 5.

FIG. 31 is a flowchart of the process of the genotype analyzer in Example 5.

The processes of steps 3101 to 3107 shown in FIG. 31 are explained below.

In the step 3101, electrophoresis of an actual sample is performed. This process is similar to the electrophoresis process in Example 1 (FIG. 7). In Example 5, the allelic ladder is treated as an actual sample.

Next, in the step 3102, the fluorescence intensities are calculated. The means for calculating the fluorescence intensities is similar to that of Example 1. In this Example, the fluorescence intensities are calculated using the initial matrix as in Example 1, when the step 3102 is the first fluorescence intensity calculation. In other words, on the supposition that the initial matrix and the fluorescence spectra for obtaining the initial matrix have been obtained in advance through measurement, the fluorescence intensity waveform of each fluorescent color is calculated by (Formula 1) using the initial matrix.

When the step 3102 is the second fluorescence intensity calculation or after that, that is, when the matrix calculation according to this Example has already been conducted, the fluorescence intensity waveform of each fluorescent color may be calculated by (Formula 1) using the matrix calculated previously (a step 3106, which will be explained below).

Next, peaks are detected from the fluorescence intensity waveforms of the fluorescent colors in the step 3103. This process is similar to that of Example 1 (the step 603 in FIG. 6).

Next, the presence or absence of a false peak is determined in the step 3104. As shown in FIG. 30 in Example 3, when the matrix used for calculating the fluorescence intensity waveforms in the step 3102 is not appropriate, a false peak may appear at the same peak position as a main peak of a fluorescent color. Thus, in the step 3104, such a false peak for each fluorescent color is searched from the peaks detected in the step 3103.

When no false peak is detected for a main peak of a fluorescent color, the fluorescence spectrum corresponding to the matrix used in the step 3102 is employed. That is, this process corresponds to the replacement of a column vector of the fluorescence spectrum matrix S of (Formula 2) corresponding to the initial matrix with the spectrum at the false peak time.

When there is no false peak for a fluorescent color, it is determined that the fluorescence spectrum is appropriate, and the spectrum of the fluorescent color is not modified. When not false peak is detected for any of the fluorescent colors, the matrix used in the step 3102 is used as the final matrix, and STR analysis in the step 3107 is conducted. The contents of the STR analysis process in the step 3107 are similar to those of Example 1.

When a false peak is detected for one or more fluorescent colors in the step 3104, the step 3105 is conducted to obtain the fluorescence spectra.

The process of the step 3105 is similar to that of Example 3, and a time at which there is a false peak is used as the single-color peak time, and the measured spectrum at this time is used as the fluorescence spectrum of the fluorescent color in the step 3105.

Then, a matrix is calculated by (Formula 3) from the obtained fluorescence spectra in the step 3106. This process is similar to that of Example 1. After this, the step 3104 is conducted again using the obtained matrix, followed by the fluorescence intensity calculation (the step 3102) and the peak detection (the step 3103), and the false peak determination (the step 3104) is conducted again. Such a set of processes is repeated until no false peak is detected anymore to update the matrix.

When the false peaks are searched properly in the step 3104, a matrix with which no false peak is detected can be generally obtained after repeating the set of processes for certain times. However, when the false peaks are not searched properly, a false peak may still be detected even when the set of processes is repeated.

For such a case, it is desirable to set an upper limit for the repetition number in practice, and when the repetition number reaches the upper limit, it is desirable to conduct a process of employing a matrix which gives the lowest level of false peaks, employing the initial matrix or the like.

Moreover, when the false peaks are searched in the step 3104, the user interface unit 103 may provide means for changing the conditions for determining the false peak and calculating the matrix again. Examples of the items of the conditions for determining the false peak are the ratio of the height of the false peak to the height of the main peak described in Example 3, the maximums and the minimums of the heights of the main peak and the false peak, the difference between the main peak time and the false peak time and the repetition number of the matrix.

Figure 33:
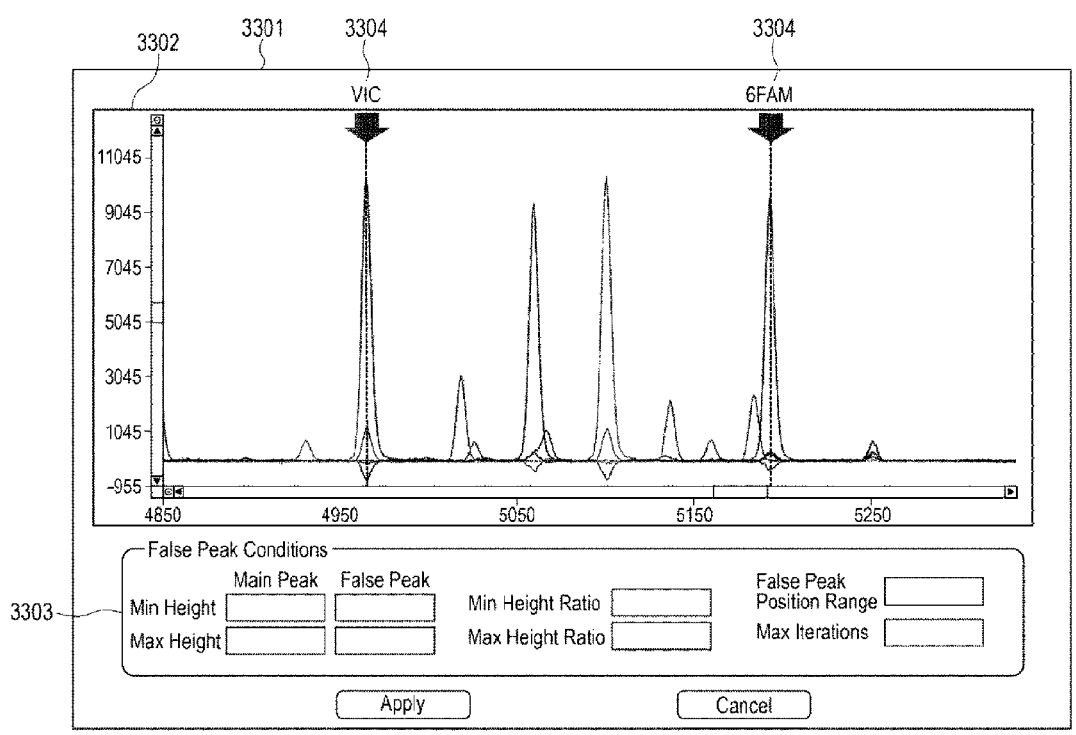
[FIG. 33] A figure showing an example user interface display of the genetic analyzer according to Example 5.

An example of the display form is shown in FIG. 33. The figure shows an example in which an area showing the overlapped fluorescence intensity waveforms of the fluorescence (3302), an area for setting the conditions for determining the false peak (3303) and the like are displayed on a screen (3301). The user may set the values using input means (such as a mouse pointer or a keyboard), which is not illustrated, in the user interface unit 103.

Moreover, in FIG. 33, the automatic calculation results of the single-color peak times of the false peak determination (3304) can be checked on the screen (3301), and the single-color peak times of the colors can be modified manually according to the need. When the user can check and modify the single-color peak times in this manner, a more stable matrix can be obtained.

As described above, the genotype analyzer according to Example 5 of the invention is characterized by performing spectral calibration by detecting the single-color peaks using the spectra obtained by electrophoresis of an actual sample for each capillary and by determining the fluorescence spectra based on the single-color peaks, instead of using the shift from the reference fluorescence spectra. Here, by searching the false peaks of the actual sample and repeatedly calculating a matrix with which no false peak is detected, a more appropriate matrix can be obtained.

Best embodiments for carrying out the invention have been explained above. However, the invention is not limited to the Examples, and modifications are acceptable within the scope of gist of the invention. For example, an electrophoresis apparatus of a microchip type having sample flow paths formed inside thereof may be used. In this case, the flow paths correspond to the capillaries in this specification. Moreover, the invention can be applied also to an electrophoresis apparatus using a slab gel.

In addition, the invention can be achieved by a program code of software achieving the functions of the Examples. In this case, a storage medium storing the program code is installed in a system or an apparatus, and the computer of the system or the apparatus (or CPU or MPU) reads the program code stored in the storage medium. In this case, the program code read from the storage medium itself achieves the functions of the Examples, and the program code itself and the storage medium storing the program code constitute the invention. As the storage medium for providing the program code, a flexible disk, a CD-ROM, a DVD-ROM, a hard disk, an optical disk, a magneto-optical disk, a CD-R, a magnetic tape, a nonvolatile memory card and ROM are used for example.

Based on the instructions of the program code, the OS (operating system) working on the computer or the like may conduct a part or all of the actual processes, and the functions of the embodiments may be achieved by the processes. Moreover, the program code read from the storage medium may be transferred to a memory on the computer. Then the CPU of the computer or the like may conduct a part or all of the actual processes based on the instructions of the program code, and the functions of the embodiments may be achieved by the processes.

Moreover, by distributing the program code of software achieving the functions of the embodiments via a network, the program code may be stored in storage means such as the hard disk or memory of a system or an apparatus or a storage medium such as a CD-RW and a CD-R, and the computer of the system or the apparatus (or CPU or MPU) may read the program code stored in the storage means or the storage medium for the use and carry out the program.

Constituent features of the invention comprehended from the embodiments are as follows.

(1) A method for genotypic analysis for calculating fluorescence intensities of DNA samples labeled with two or more fluorescent dyes based on spectra obtained by electrophoresis means which irradiates a flow path array containing two or more flow paths with excitation light, separates light emitted from the flow path array and images spectra on a light detector; characterized by determining reference fluorescence spectra of the fluorescent dyes based on the spectra obtained by the electrophoresis of the DNA samples and shifting the reference fluorescence spectra in the wavelength direction to determine the fluorescence spectra of the flow paths.

(2) The method for genotypic analysis of (1) characterized by determining the reference fluorescence spectra by extracting single spectra of light emitted from the fluorescent dyes from the spectra of a sample containing DNA fragments with known lengths.

(3) The method for genotypic analysis of (1) characterized in that ideal fluorescence spectra which are measured in advance are used as the reference fluorescence spectra.

(4) The method for genotypic analysis of (2) characterized in that the reference fluorescence spectra are corrected referring to ideal fluorescence spectra which are measured in advance.

(5) The method for genotypic analysis of (1) characterized by determining the reference fluorescence spectra by extracting single spectra of light emitted from the fluorescent dyes from spectra of an actual sample which is a subject of the genotype analysis.

(6) The method for genotypic analysis of any one of (1) to (5) characterized by determining a shift amount of fluorescence spectra of flow paths in the wavelength direction by extracting single fluorescence spectra of the fluorescent dye labeling a size standard for the flow paths and shifting the reference fluorescence spectra by the shift amount.

(7) The method for genotypic analysis of any one of (1) to (5) characterized by determining a shift amount of fluorescence spectra of flow paths in the wavelength direction by measuring Raman spectra of the flow paths and shifting the reference fluorescence spectra by the shift amount.

(8) The method for genotypic analysis of (1) characterized by determining whether or not a single spectrum of light emitted from one fluorescent dye can be extracted from spectra of an actual sample which is a subject of the genotype analysis and determining the fluorescence spectra by shifting the reference fluorescence spectra when the determination is negative.

(9) A device for genotypic analysis having: a light source applying excitation light; an electrophoresis apparatus having a flow path array containing two or more flow paths, a voltage source applying voltage to both ends of the flow path array and a light detector detecting light emitted from the flow path array; and a data analyzer sending information to and receiving information from the electrophoresis apparatus:

characterized by introducing DNA samples containing DNA fragments labeled with two or more fluorescent dyes to the flow path array, irradiating the flow path array with the excitation light from the light source while moving the DNA fragments through the flow path array using the voltage source, separating light emitted from the flow path array by the irradiation and imaging spectra on the light detector, determining reference fluorescence spectra of the fluorescent dyes based on the imaged spectra in the data analyzer, and determining fluorescence spectra of the flow paths by shifting the reference fluorescence spectra in the wavelength direction.

(10) The device for genotypic analysis of (9) characterized by determining the reference fluorescence spectra and determining the fluorescence spectra of the flow paths by shifting the reference fluorescence spectra in the wavelength direction.

(11) The device for genotypic analysis of (9) characterized by determining the reference fluorescence spectra by extracting single spectra of light emitted from the fluorescent dyes from spectra of a sample containing DNA fragments with known lengths.

(12) The device for genotypic analysis of (9) characterized in that ideal fluorescence spectra which are measured in advance are used as the reference fluorescence spectra.

(13) The device for genotypic analysis of (10) characterized in that the reference fluorescence spectra are corrected referring to ideal fluorescence spectra which are measured in advance.

(14) The device for genotypic analysis of (9) characterized by determining the reference fluorescence spectra by extracting single spectra of light emitted from the fluorescent dyes from spectra of an actual sample which is a subject of the genotype analysis.

(15) The device for genotypic analysis of any one of (9) to (14) characterized by determining a shift amount of fluorescence spectra of flow paths in the wavelength direction by extracting single fluorescence spectra of the fluorescent dye labeling a size standard for the flow paths and shifting the reference fluorescence spectra by the shift amount.

(16) The device for genotypic analysis of any one of (9) to (14) characterized by determining a shift amount of fluorescence spectra of flow paths in the wavelength direction by measuring Raman spectra of the flow paths and shifting the reference fluorescence spectra by the shift amount.

REFERENCE SIGNS LIST

101: genotype analyzer (or device for genotypic analysis)
102: Central control unit
103: User interface unit
104: Storage unit
105: Electrophoresis apparatus
106: Sample information setting unit
107: Peak detection unit
108: Electrophoresis apparatus control unit
109: Matrix calculation unit
110: Fluorescence intensity calculation unit
111: STR analysis unit
112: Data analyzer

The invention claimed is:

1. A method for genotypic analysis characterized by
introducing a DNA sample containing DNA fragments labeled with two or more fluorescent dyes to a flow path array containing two or more flow paths,
irradiating the DNA fragments with excitation light while moving the DNA fragments through the flow path array using electrophoresis means,
calculating fluorescence intensity waveforms of the DNA fragments based on spectra obtained by separating light emitted from the flow path array by the irradiation, and
determining fluorescence spectra of the fluorescent dyes based on the calculated fluorescence intensity waveforms.

2. The method for genotypic analysis described in claim 1, characterized by
preparing an actual sample which is a subject of the genotype analysis as the DNA sample,
extracting a spectrum of light emitted from one fluorescent dye from the spectra of the actual sample obtained by the separation and determining the fluorescence spectra based on the extracted spectrum.

3. The method for genotypic analysis described in claim 2, characterized by extracting the spectrum of light emitted from one fluorescent dye by searching a false peak of the fluorescence intensity waveforms.

4. The method for genotypic analysis described in claim 3, characterized by repeating the false peak search and the calculation of the fluorescence intensity waveforms until the condition that the false peak is not detected or the condition that a repetition number reaches a set upper limit is met.

5. The method for genotypic analysis described in claim 2, characterized in that the fluorescence spectra are fluorescence spectra which are determined previously.

6. The method for genotypic analysis described in claim 5, characterized in that
a detection condition of the false peak or a detection result of the false peak is displayed during the false peak search and a user can modify the detection condition or the detection result referring to the display.

7. A device for genotypic analysis having
a light source applying excitation light,
an electrophoresis apparatus having a flow path array containing two or more flow paths, a voltage source applying voltage to both ends of the flow path array and a light detector detecting light emitted from the flow path array, and
a data analyzer sending information to and receiving information from the electrophoresis apparatus,
characterized by
introducing a DNA sample containing DNA fragments labeled with two or more fluorescent dyes to the flow path array,
irradiating the flow path array with the excitation light from the light source while moving the DNA fragments through the flow path array using the voltage source,
separating light emitted from the flow path array by the irradiation and imaging spectra on the light detector, and
calculating fluorescence intensity waveforms of the DNA fragments based on the imaged spectra with the data analyzer and determining fluorescence spectra of the fluorescent dyes based on the calculated fluorescence intensity waveforms.

8. The device for genotypic analysis described in claim 7, characterized in that
an actual sample which is a subject of the genotype analysis is used as the DNA sample, and
a spectrum of light emitted from one fluorescent dye is extracted from the spectra of the actual sample obtained by the separation and the fluorescence spectra are determined based on the extracted spectrum with the data analyzer.

9. The device for genotypic analysis described in claim 8, characterized by extracting the spectrum of light emitted from one fluorescent dye by searching a false peak of the fluorescence intensity waveforms with the data analyzer.

10. The device for genotypic analysis described in claim 9, characterized by repeating the false peak search and the calculation of the fluorescence intensity waveforms until the condition that the false peak is not detected or the condition that a repetition number reaches a set upper limit is met with the data analyzer.

11. The device for genotypic analysis described in claim 8, characterized in that the fluorescence spectra are fluorescence spectra which are determined previously.

12. The device for genotypic analysis described in claim 11, characterized in that a detection condition of the false peak or a detection result of the false peak is displayed during the false peak search with the data analyzer and a user can modify the detection condition or the detection result referring to the display.

* * * * *